(12) United States Patent
Funayama

(10) Patent No.: US 10,716,804 B2
(45) Date of Patent: Jul. 21, 2020

(54) CROSSLINKED CHONDROITIN SULFATE, COMPOSITION CONTAINING SAME, AND TREATMENT AGENT FOR EYE DISEASE

(71) Applicant: SEIKAGAKU CORPORATION, Tokyo (JP)

(72) Inventor: Sho Funayama, Tokyo (JP)

(73) Assignee: SEIKAGAKU CORPORATION, Tokyo (JP)

( * ) Notice: Subject to any disclaimer, the term of this patent is extended or adjusted under 35 U.S.C. 154(b) by 0 days.

(21) Appl. No.: 16/536,779

(22) Filed: Aug. 9, 2019

(65) Prior Publication Data
US 2019/0365796 A1    Dec. 5, 2019

Related U.S. Application Data

(63) Continuation of application No. 15/543,748, filed as application No. PCT/JP2016/051176 on Jan. 15, 2016, now Pat. No. 10,420,796.

(30) Foreign Application Priority Data

Jan. 16, 2015  (JP) ................... 2015-007072
Jul. 30, 2015  (JP) ................... 2015-150976

(51) Int. Cl.
| A61K 31/738 | (2006.01) |
| A61P 27/02  | (2006.01) |
| A61K 9/00   | (2006.01) |
| A61K 9/08   | (2006.01) |

(52) U.S. Cl.
CPC .......... *A61K 31/738* (2013.01); *A61K 9/0048* (2013.01); *A61K 9/08* (2013.01); *A61P 27/02* (2018.01)

(58) Field of Classification Search
CPC .................................................. A61K 31/738
See application file for complete search history.

(56) References Cited

U.S. PATENT DOCUMENTS

| 4,863,907 | A | 9/1989 | Sakurai et al. |
| 5,525,634 | A | 6/1996 | Sintov et al. |
| 5,527,893 | A | 6/1996 | Burns et al. |
| 5,830,913 | A | 11/1998 | Ogawa et al. |
| 5,866,619 | A | 2/1999 | Sintov et al. |
| 2017/0362347 | A1* | 12/2017 | Karlsson .............. B01J 13/0052 |

FOREIGN PATENT DOCUMENTS

| EP | 0 774 254 | 5/1997 |
| JP | 06-73102 | 3/1994 |
| JP | 07-223966 | 8/1995 |
| JP | 09-136832 | 5/1997 |
| JP | 2000-319194 | 11/2000 |
| JP | 2002-529549 | 9/2002 |
| WO | 91/16881 | 11/1991 |
| WO | WO2000/027886 | 5/2000 |
| WO | 2008/070640 | 6/2008 |

OTHER PUBLICATIONS

Micheal A. Lemp, et al., "The Definition and Classification of Dry Ey Disease: Report of the Definition and Classification Subcommittee of the International Dry Eye WorkShop", The Ocular Surface, vol. 5, No. 2, Apr. 2007, pp. 75-95.
Tsutomu Fujihara et al., "Establishment of a Rabbit Short-Term Dry Eye Model", Journal of Ocular Pharmacology and Therapeutics, vol. 11, No. 4, 1995, pp. 503-508.
Gary D. Novack, "Why Aren't There More Phramacotherapies for Dry Eye?", The Ocular Surface, vol. 12, No. 3, Jul. 2014, pp. 227-230.
Teruo Nishida et al., "Hyaluronan Stimulates Corneal Epithelial Migration", Experimental Eye Research, vol. 53, 1991, pp. 753-758.
Amnon Sintov et al., "Cross-linked chondroitin sulphate: characterization for drug delivery purposes", Biomaterials vol. 16, No. 6, 1995, pp. 473-478.
C. Bourie et al., "Insolubilization Test of Sodium Chondroitin Sulphate with a View to Its Use as Colonic Carrier of Drugs", Journal of Biomaterials Applications, vol. 12, 1998, pp. 201-221.
Michael B. Limberg, M.D. et al., "Topical Application of Hyaluronic Acid and Chondroitin Sulfate in the Treatment of Dry Eyes", American Journal of Ophthalmology, vol. 103, No. 2, Feb. 1987, pp. 194-197.
Abraham Rubinstein et al., "Chondroitin sulfate: A potential biodegradable carrier for colon-specific drug delivery", International Journal of Pharmaceutics, vol. 84, No. 2, Jul. 31, 1992, pp. 141-150.
Yutaka Okano, "Tokushu Sijoegren Shokogun no Atarashii Wadai V. Chiryo", Prog. Med., vol. 22, No. 1, Jan. 2002, pp. 57-62.
International Search Report issued in WIPO Patent Application No.
Supplementary European Search Report in Application No. EP 16737468 dated Jun. 7, 2018.
Strehin et al., "Synthesis and characterization of chondroitin sulfate-polyethylene glycol corneal adhesive," J. Caratract Refract. Surg. 2009, vol. 35, pp. 567-576.
EMD Millipore Sterile filtration pamphlet, 2012, EMD Millipore Corporation, 2012.
Notice of Reasons of Refusal, Japanese Patent Office, Application No. 2017-043621, dated Jan. 8, 2020, English translation.

* cited by examiner  PCT/JP2016/051176, dated Mar. 29, 2016.

*Primary Examiner* — Jonathan S Lau
(74) *Attorney, Agent, or Firm* — Greenblum & Bernstein, P.L.C.

(57) ABSTRACT

Provided is a chondroitin sulfate derivative having a crosslinked structure through a group in a polyvalent amine. Also provided is a composition containing the chondroitin sulfate derivative. Also provided are an agent and method for the treatment of an eye disease, the agent and method having a therapeutic effect on a corneal epithelial disorder and/or dry eye.

9 Claims, 10 Drawing Sheets

Average + standard error, *p<0.05, **p<0.01 (vs PBS), #p<0.05 (vs 2% CS)

Average + standard error, *p<0.05, **p<0.01 (vs PBS)

Average + standard error, **p<0.01 (vs PBS)

CROSSLINKED CHONDROITIN SULFATE, COMPOSITION CONTAINING SAME, AND TREATMENT AGENT FOR EYE DISEASE

This application is a Continuation of U.S. patent application Ser. No. 15/543,748, filed Jul. 14, 2017, which is the National Stage of International Patent Application No. PCT/JP2016/051176, filed Jan. 15, 2016, which claims the benefit of priority of Japanese Application No. 2015-007072, filed Jan. 16, 2015 and Japanese Application No. 2015-150976, filed Jul. 30, 2015. The disclosures of each of these documents, including the specifications, drawings and claims, are incorporated herein by reference in their entirety.

TECHNICAL FIELD

The present invention relates to a cross-linked chondroitin sulfate, to a composition containing the same, and to an agent for the treatment of an eye disease.

BACKGROUND ART

According to the international Dry Eye Workshop (DEWS), "dry eye" is defined as follows: "Dry eye is a multifactorial disease of the tears and ocular surface that results in symptoms of discomfort, visual disturbance, and tear film instability with potential damage to the ocular surface. It is accompanied by increased osmolarity of the tear film and inflammation of the ocular surface" (The Ocular Surface Vol. 5, No. 2: 75-92, 2007).

An eye drop (Chondron (registered trademark)) containing chondroitin sulfate (hereinafter may be referred to as "CS") has been known in Japan, and the eye drop has the effect of "protecting the superficial cornea." Studies on the effect of CS on the ocular surface (Tsutomu Fujihara, et al., Journal of Ocular Pharmacology and Therapeutics, Vol. 11, No. 4: 503-508, 1995) have reported the examination of the prevention of corneal epithelial disorders. Teruo Nishida, et al., Experimental Eye Research, 53: 753-758, 1991 describes the examination of the presence or absence of the effect of CS on corneal epithelial cells. The recent literature Gary D. Novack, The Ocular Surface, Vol. 12, No. 3: 227-230, 2014 describes a variety of therapeutic agents for dry eye developed in Japan and the U.S.

Regarding CS derivatives having a cross-linked structure through a cross-linker (hereinafter such a derivative may be referred to as "cross-linked CS") (WO 1991/16881, pamphlet, Japanese Patent Application Laid-Open (kokai) No. 1994-73102, Amnon Sintov, et al., Biomaterials, 16: 473-478, 1995), Rubinstein, et al. have reported attempts to produce CS derivatives using 1,12-diaminododecane as a cross-linker (WO 1991/16881, pamphlet, Amnon Sintov, et al., Biomaterials, 16: 473-478, 1995). In the field of CS, CS (which is readily water-soluble) is cross-linked for imparting poor water-solubility thereto, for use as, for example, membranes or tablets.

PRIOR ART DOCUMENTS

Patent Documents

Patent Document 1: WO 1991/16881, pamphlet
Patent Document 2: Japanese Patent Application Laid-Open (kokai) No. 1994-73102

Non-Patent Documents

Non-Patent Document 1: The Ocular Surface Vol. 5, No. 2: 75-92, 2007

Non-Patent Document 2: Tsutomu Fujihara, et al., Journal of Ocular Pharmacology and Therapeutics, Vol. 11, No. 4: 503-508, 1995
Non-Patent Document 3: Teruo Nishida, et al., Experimental Eye Research, 53: 753-758, 1991
Non-Patent Document 4: Gary D. Novack, The Ocular Surface, Vol. 12, No. 3: 227-230, 2014
Non-Patent Document 5: Amnon Sintov, et al., Biomaterials, 16: 473-478, 1995
Non-Patent Document 6: C. Bourie, et al., Journal of Biomaterials Applications, Vol. 12: 201-221, 1998

SUMMARY OF THE INVENTION

Problems to be Solved by the Invention

However, Journal of Ocular Pharmacology and Therapeutics, Vol. 11, No. 4: 503-508, 1995 does not disclose the treatment for developed corneal epithelial disorders. Experimental Eye Research, 53: 753-758, 1991 describes that CS does not have the effect on migration of corneal epithelial cells. The Ocular Surface, Vol. 12, No. 3: 227-230, 2014 does not describe a therapeutic agent containing CS as an active pharmaceutical ingredient.

The cross-linking of CS was not confirmed by various analytical methods and production methods described in WO 1991/16881, pamphlet or Biomaterials, 16: 473-478, 1995 (C. Bourie, et al., Journal of Biomaterials Applications, Vol. 12: 201-221, 1998). Therefore, it was revealed that no cross-linked CS has been practically produced.

In view of the foregoing, an object of the present invention is to provide a CS derivative having a cross-linked structure through a group in a polyvalent amine. Another object of the present invention is to provide a composition containing the CS derivative. Still another object of the present invention is to provide an agent for the treatment of an eye disease, the agent having a therapeutic effect on a corneal epithelial disorder and/or dry eye. Yet another object of the present invention is to provide a method for the treatment of an eye disease, the method being therapeutically effective on a corneal epithelial disorder and/or dry eye. The present invention achieves at least one of these objects.

Means for Solving the Problems

The present inventors have first successfully produced a CS derivative having a cross-linked structure through a group in a polyvalent amine and have accomplished the present invention. The inventors have unexpectedly found that a composition containing cross-linked CS can be used in the form of a solution, contrary to the conventional knowledge that CS is cross-linked for imparting poor water solubility thereto. The inventors have also found that the composition exhibits an excellent therapeutic effect on a corneal epithelial disorder and/or dry eye. The present invention has been accomplished on the basis of these findings.

The present invention includes the following embodiments.

[A1] A chondroitin sulfate derivative having a cross-linked structure through a cross-linker, the derivative being cross-linked between disaccharide units of chondroitin sulfate.

[A2] The chondroitin sulfate derivative according to [A1], wherein the cross-linker is a residue derived from at least one species selected from the group consisting of a polyvalent amine, a polyvalent epoxy compound, a polyvalent vinyl compound, and an epihalohydrin.

[A3] The chondroitin sulfate derivative according to [A1] or [A2], wherein the cross-linker is a residue derived from a polyvalent amine

[A4] The chondroitin sulfate derivative according to [A3], wherein the polyvalent amine is a polyvalent amine having no biodegradable moiety in the main chain.

[A5] The chondroitin sulfate derivative according to [A3] or [A4], wherein the polyvalent amine is a polyvalent amine having no disulfide bond in the main chain.

[A6] The chondroitin sulfate derivative according to any of [A3] to [A5], wherein the polyvalent amine is a substituted or unsubstituted polyvalent amine having 1 to 20 carbon atoms in the main chain and optionally having a heteroatom in the main chain.

[A7] The chondroitin sulfate derivative according to any of [A3] to [A5], wherein the polyvalent amine is a substituted or unsubstituted polyvalent amine having 1 to 20 atoms in the main chain and optionally having a heteroatom in the main chain.

[A8] The chondroitin sulfate derivative according to any of [A3] to [A7], wherein the polyvalent amine is an aliphatic polyvalent amine

[A9] The chondroitin sulfate derivative according to any of [A3] to [A8], wherein the polyvalent amine is a diamine.

[A10] The chondroitin sulfate derivative according to any of [A3] to [A7], wherein the polyvalent amine is at least one species selected from the group consisting of ethane-1,2-diamine, 1,3-diaminopropane, 1,4-diaminobutane, 1,5-diaminopentane, 1,6-diaminohexane, 1,8-diaminooctane, 1,12-diaminododecane, spermidine, L-lysine ethyl ester, L-ornithine ethyl ester, 1,3-diamino-2-propanol, 2-(aminomethyl)-2-methylpropane-1,3-diamine, (E)-2-butene-1,4-diamine, 1,4-bis(aminomethyl)benzene, 1,4-bis(aminomethyl)cyclohexane, 2,2'-thiodiethanamine, 2,2'-oxydiethanamine, 1,11-diamino-3,6,9-trioxaundecane, and salt forms thereof.

[A11] The chondroitin sulfate derivative according to any of [A1] to [A10], wherein the structure is represented by the following formula (I):

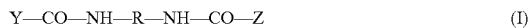

Y—CO—NH—R—NH—CO—Z  (I)

(where Y—CO— represents a disaccharide unit moiety in a chondroitin sulfate molecule;
—CO—Z represents a disaccharide unit moiety in the same chondroitin sulfate molecule or a different chondroitin sulfate molecule;
R represents a substituted or unsubstituted hydrocarbon group optionally having a heteroatom in the main chain; and
—CO—NH— and —NH—CO— each represent an amide bond formed between an amino group of a polyvalent amine and a carboxy group of a glucuronic acid, which is a constitutive sugar moiety in chondroitin sulfate).

[A12] The chondroitin sulfate derivative according to [A11], wherein R in the formula (I) has no biodegradable moiety in the main chain.

[A13] The chondroitin sulfate derivative according to [A11] or [A12], wherein R in the formula (I) has no disulfide bond in the main chain.

[A14] The chondroitin sulfate derivative according to any of [A11] to [A13], wherein R in the formula (I) represents a substituted or unsubstituted hydrocarbon group optionally having a heteroatom in the main chain;
the heteroatom is one to three atoms selected from the group consisting of nitrogen, oxygen, and sulfur; and
the substituted hydrocarbon group has at least one substituent selected from the group consisting of a C1 to C3 alkyl group, a C1 to C3 aminoalkyl group, a C1 to C3 hydroxyalkyl group, a C1 to C3 alkyl ester group, a C1 to C3 alkoxy group, an amino group, a formyl group, a hydroxy group, and a carboxy group.

[A15] The chondroitin sulfate derivative according to any of [A11] to [A14], wherein the hydrocarbon group has 1 to 20 carbon atoms in the main chain.

[A16] The chondroitin sulfate derivative according to any of [A11] to [A14], wherein the hydrocarbon group has 1 to 10 carbon atoms in the main chain.

[A17] The chondroitin sulfate derivative according to any of [A11] to [A14], wherein the hydrocarbon group has 1 to 8 carbon atoms in the main chain.

[A18] The chondroitin sulfate derivative according to any of [A11] to [A14], wherein the hydrocarbon group has 1 to 20 atoms in the main chain.

[A19] The chondroitin sulfate derivative according to any of [A11] to [A14], wherein the hydrocarbon group has 1 to 11 atoms in the main chain.

[A20] The chondroitin sulfate derivative according to any of [A11] to [A14], wherein the hydrocarbon group has 1 to 8 atoms in the main chain.

[A21] The chondroitin sulfate derivative according to any of [A11] to [A20], wherein the hydrocarbon group is an aliphatic hydrocarbon group.

[A22] The chondroitin sulfate derivative according to any of [A1] to [A21], which has water solubility.

[A23] A composition comprising the chondroitin sulfate derivative as recited in any of [A1] to [A22] and a pharmaceutically acceptable carrier.

[A24] The composition according to [A23], which is in the form of an aqueous solution.

[A25] The composition according to [A23] or [A24], which passes through a porous filter (pore size: 5.0 μm, diameter: 25 mm) at a passing rate of 80% or more at 25° C.

[A26] The composition according to any of [A23] to [A25], which has a viscosity of 5 to 11,000 mPa·s.

[A27] The composition according to any of [A23] to [A26], wherein the amount of the chondroitin sulfate derivative is 0.1 to 15 wt. % on the basis of the entire amount of the composition.

[A28] A pharmaceutical preparation comprising the chondroitin sulfate derivative as recited in any of [A1] to [A22].

[A29] The composition according to any of [A23] to [A27], which serves as an agent for the treatment of an eye disease.

[A30] The composition according to any of [A23] to [A27], which serves as an agent for the treatment of a corneal epithelial disorder.

[A31] The composition according to any of [A23] to [A27], which serves as an agent for the treatment of dry eye.

[B1] An agent for the treatment of an eye disease, the agent comprising the chondroitin sulfate derivative as recited in any of [A1] to [A22] as an active pharmaceutical ingredient.

[B2] The agent for the treatment of an eye disease according to [B1], which serves as an eye drop.

[B3] The agent for the treatment of an eye disease according to [B1] or [B2], which serves as an aqueous eye drop.

[B4] The agent for the treatment of an eye disease according to any of [B1] to [B3], which is in the form of an aqueous solution.

[B5] The agent for the treatment of an eye disease according to any of [B1] to [B4], which passes through a porous filter (pore size: 5.0 μm, diameter: 25 mm) at a passing rate of 80% or more at 25° C.

[B6] The agent for the treatment of an eye disease according to any of [B1] to [B5], wherein the eye disease is a corneal epithelial disorder.
[B7] The agent for the treatment of an eye disease according to any of [B1] to [B5], wherein the eye disease is dry eye.
[B8] The agent for the treatment of an eye disease according to any of [B1] to [B7], wherein the treatment is therapy.
[C1] A method for the treatment of an eye disease, the method comprising a step of instilling the composition as recited in any of [A23] to [A27] to an eye of a subject in need thereof.
[C2] The method according to [C1], wherein the composition is instilled into the eye by instillation.
[C3] The method according to [C1] or [C2], wherein the composition serves as an aqueous eye drop.
[C4] The method according to any of [C1] to [C3], wherein the composition is in the form of an aqueous solution.
[C5] The method according to any of [C1] to [C4], wherein the composition passes through a porous filter (pore size: 5.0 μm, diameter: 25 mm) at a passing rate of 80% or more at 25° C.
[C6] The method according to any of [C1] to [C5], wherein the eye disease is a corneal epithelial disorder.
[C7] The method according to any of [C1] to [C5], wherein the eye disease is dry eye.
[C8] The method according to any of [C1] to [C7], wherein the treatment is therapy.

Advantageous Effects of the Invention

In one aspect, the present invention provides a CS derivative having a cross-linked structure through a group in a polyvalent amine. In another aspect, the present invention provides a composition containing the cross-linked CS derivative (hereinafter referred to as "cross-linked CS"). In still another aspect, the present invention provides an agent for the treatment of an eye disease, the agent having a therapeutic effect on a corneal epithelial disorder and/or dry eye. In yet another aspect, the present invention provides a method for the treatment of an eye disease.

MODES FOR CARRYING OUT THE INVENTION

Figure 1:
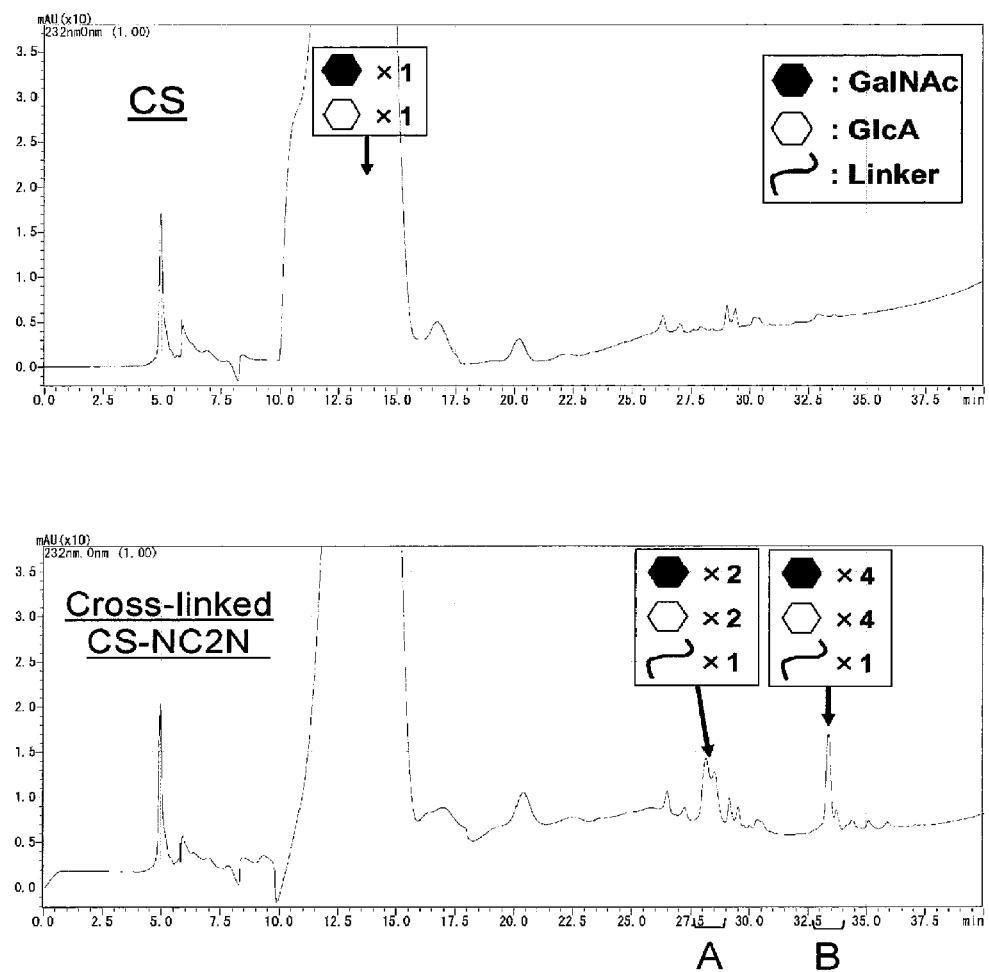
FIG. 1 shows HPLC charts of chondroitinase-ABC-digested liquids.

Terms as used herein will now be defined as follows. The term "chondroitin sulfate" (may be referred to as "CS") refers to chondroitin sulfate or a salt form thereof. The term "cross-linked chondroitin sulfate" (may be referred to as "cross-linked CS") refers to a CS derivative or a salt form thereof having a cross-linked structure through a cross-linker, the derivative being cross-linked between disaccharide units of CS. The derivative may be cross-linked within a single CS molecule and/or between different CS molecules.

As used herein, the term "substitution" refers to substitution of one or more hydrogen atoms in a compound by another atom or a group of atoms. The atom or group of atoms substituted for the hydrogen atom(s) will be referred to as "substituent." The term "heteroatom" refers to an atom (other than carbon and hydrogen) contained in a compound, such as nitrogen, oxygen, or sulfur. Unless otherwise specified, the expression "having a heteroatom" refers to the case where a compound has one or more types of heteroatoms, and one or more atoms of each type are present in the compound. The expression "having a heteroatom in a chain" refers to the case where at least one carbon atom in the chain is substituted by a heteroatom. The term "carbon chain" refers to an atomic chain mainly formed of carbon atoms, the chain optionally having a branch and/or a heteroatom. The term "reactive functional group" refers to a functional group having reactivity with a functional group contained in chondroitin sulfate. Unless otherwise specified, the term "main chain" refers to a linear carbon chain which links two reactive functional groups. When three or more reactive functional groups are present, the main chain is the longest one of linear carbon chains each linking two reactive functional groups. When the carbon chain has a branch, unless otherwise specified, a carbon chain of a branch is not included in the main chain. The main chain may have one or more heteroatoms at any position of a carbon atom other than a position at which the carbon atom is directly bonded to a reactive functional group. When a cyclic structure is present in a carbon chain linking reactive functional groups, the cyclic structure is regarded as having at least one branch and sharing an atom as a terminal of at least two branched carbon chains. In this case, the main chain is the longest chain among each of the branched chains. As used herein, the "number of atoms in a main chain" refers to the number of atoms constituting the main chain. In the case where the main chain has a heteroatom, the number of atoms in the main chain includes the number of the heteroatom. As used herein, the "main chain" of a polyvalent amine or a group in a polyvalent amine refers to a linear carbon chain linking two primary amino groups, which are reactive functional groups.

As used herein, the term "hydrocarbon" refers to, for example, a group or compound having carbon and hydrogen. Unless otherwise specified, the hydrocarbon may have a heteroatom and/or a substituent. The "hydrocarbon" may have a linear or branched structure. The term "aliphatic" refers to, for example, a group or compound having no aromaticity. The term "cyclic" refers to, for example, a group or compound having an intramolecular cyclic structure. The term "acyclic" refers to, for example, a group or compound having no intramolecular cyclic structure. The term "alkyl group" refers to a monovalent linear or branched saturated aliphatic hydrocarbon group. The term "alkylene group" refers to a divalent linear or branched saturated aliphatic hydrocarbon group. The term "alkenylene group" refers to a divalent linear or branched unsaturated aliphatic hydrocarbon group having at least one double bond. The term "alkynylene group" refers to a divalent linear or branched unsaturated aliphatic hydrocarbon group having at least one triple bond. The term "aryl group" refers to a monovalent monocyclic or polycyclic aromatic hydrocarbon group. The term "arylene group" refers to a divalent monocyclic or polycyclic aromatic hydrocarbon group. The term "arylalkylene group" refers to a divalent group formed through substitution of one hydrogen atom of an aryl group by an alkylene group, or a divalent group formed through substitution of two hydrogen atoms of an aromatic ring by alkylene groups. The term "cycloalkyl group" refers to a monovalent cyclic aliphatic hydrocarbon group. The term "cycloalkylene group" refers to a divalent cyclic aliphatic hydrocarbon group. The term "cycloalkylalkylene group" refers to a divalent group formed through substitution of one hydrogen atom of a cycloalkyl group by an alkylene group, or a divalent group formed through substitution of two hydrogen atoms of a cycloalkane by alkylene groups. The term "aminoalkyl group" refers to an amino-substituted alkyl group. The term "hydroxyalkyl group" refers to a hydroxy-substituted alkyl group.

As used herein, the term "polyvalent amine" refers to an amine having two or more primary amino groups (—$NH_2$). As used herein, the term "diamine" refers to an amine having two primary amino groups, and the term "triamine" refers to an amine having three primary amino groups.

As used herein, the term "aliphatic polyvalent amine" refers to a polyvalent amine formed through substitution of two or more hydrogen atoms of an aliphatic hydrocarbon by primary amino groups. The term "aromatic polyvalent amine" refers to a polyvalent amine formed through substitution of two or more hydrogen atoms of an aromatic hydrocarbon by primary amino groups or aminoalkyl groups.

As used herein, the term "to" between two numerical values indicates that the numerical values before and after the term mean the lower limit value and the upper limit value in the range, respectively. When a composition contains some kind of components, the content of the component in the composition refers to the total amount of the components in the composition, unless otherwise specified.

The present invention will next be described in more detail with reference to embodiments, which should not be construed as limiting the invention thereto.

<Cross-Linked CS>

The "cross-linked CS" of the present invention has a cross-linked structure between disaccharide units of CS through a cross-linker. The cross-linked CS may be cross-linked within a single CS molecule and/or between different CS molecules. No particular limitation is imposed on the type of CS used as a raw material for producing the cross-linked CS, so long as the CS is a glycosaminoglycan that has a primary structure formed of repeating disaccharide units of D-glucuronic acid and N-acetyl-D-galactosamine wherein hydroxy groups of the constitutive sugars are partially sulfated. The cross-linked CS and CS used as a raw material therefor may be in a free (non-salt) form or a pharmaceutically acceptable salt form.

Examples of the pharmaceutically acceptable salt include an alkali metal, such as a sodium salt and a potassium salt; and an alkaline earth metal salt, such as a magnesium salt and a calcium salt. The cross-linked CS of the present invention is preferably in the form of a pharmaceutically acceptable alkali metal salt, more preferably in the form of a sodium salt, from the viewpoints of biological compatibility and affinity.

The cross-linked CS of the present invention or CS used as a raw material therefor may be in the form of a hydrate or a solvate.

No particular limitation is imposed on the type of CS used as a raw material for producing the cross-linked CS, and the CS may be, for example, chondroitin sulfate C (hereinafter may be referred to as "CSC"). No particular limitation is imposed on the origin of CS used as a raw material for producing the cross-linked CS. The CS may be a naturally occurring substance or may be a chemically synthesized substance. In the case where CS is obtained from, for example, a naturally occurring product, the naturally occurring product (i.e., raw material) may be appropriately selected depending on the type of CS of interest and so on. Alternatively, CS of interest may be prepared through appropriate modification of a naturally occurring substance by a chemosynthetic technique.

No particular limitation is imposed on the weight average molecular weight of CS used as a raw material for producing the cross-linked CS. The weight average molecular weight of CS is preferably 10,000 to 100,000, more preferably 10,000 to 80,000, still more preferably 10,000 to 60,000, particularly preferably 15,000 to 45,000. The weight average molecular weight of CS can be determined by a common technique, such as size exclusion chromatography or a light scattering method.

The cross-linked CS can be produced through covalent bonding between CS and a cross-linking agent.

<Cross-Linker>

As used herein, the term "cross-linker" refers to a residue derived from a compound having two or more groups capable of covalently bonding to the groups contained in CS. Such a compound preferably has at least one group selected from the group consisting of an amino group, an epoxy group, a vinyl group, and a haloalkyl group, wherein the number of the selected group(s) is two or more. The cross-linked CS of the present invention is preferably a cross-linked form with such a group. The compound having two or more groups capable of covalently bonding to the groups contained in CS is more preferably at least one compound selected from the group consisting of polyvalent amines, polyvalent epoxy compounds, polyvalent vinyl compounds, and epihalohydrins.

No particular limitation is imposed on the number of carbon atoms of the cross-linker used in the present invention or the number of carbon atoms of the polyvalent amine, polyvalent epoxy compound, polyvalent vinyl compound, and epihalohydrin used in the present invention. The number of the carbon atoms is, for example, 1 to 20, 1 to 12, 1 to 10, 1 to 8, 1 to 6, 1 to 4, 2 to 12, 2 to 10, 2 to 8, 2 to 6, 2 to 4, 4 to 12, 4 to 10, or 4 to 8.

The amino group can form an amide bond with the carboxy group of CS. The epoxy group, the vinyl group, or the haloalkyl group can form an ether bond with a hydroxy group of CS. CS has only one carboxy group in the disaccharide unit moiety. Thus, the cross-linker preferably has an amine group, and is particularly preferably a polyvalent amine, in order to reduce the structural diversity of the cross-linked CS. No particular limitation is imposed on the polyvalent amine, so long as it has two or more primary amino groups (—$NH_2$). The polyvalent amine may be, for example, a triamine or a diamine. The polyvalent amine is preferably a diamine for reducing the structural diversity of the cross-linked CS.

In the present invention, the polyvalent amine may be a polyvalent amine having no biodegradable bond (i.e., no biodegradable moiety). In the present invention, the polyvalent amine may be a polyvalent amine having no biodegradable moiety in the main chain of the molecule. As used herein, the term "biodegradable moiety" refers to a structure represented by the following formula (II):

$$—C(=O)—D— \quad (II)$$

(where D represents an oxygen atom or a sulfur atom). Specifically, the biodegradable moiety corresponds to an ester bond or a thioester bond. Thus, in the present invention, the polyvalent amine may be a polyvalent amine having neither an ester bond nor a thioester bond in the main chain of the molecule.

In the present invention, the polyvalent amine may be a polyvalent amine having no disulfide bond. The polyvalent amine may be a polyvalent amine having no disulfide bond in the main chain.

In the present invention, the polyvalent amine may be, for example, an aliphatic polyvalent amine or an aromatic polyvalent amine, but is preferably an aliphatic polyvalent amine. The aliphatic polyvalent amine may be an acyclic aliphatic polyvalent amine or a cyclic aliphatic polyvalent amine, but is preferably an acyclic aliphatic polyvalent amine. The aliphatic polyvalent amine may be a saturated aliphatic polyvalent amine or an unsaturated aliphatic polyvalent amine That is, the aliphatic polyvalent amine may be an acyclic saturated aliphatic polyvalent amine, an acyclic unsaturated aliphatic polyvalent amine, a cyclic saturated aliphatic polyvalent amine, or a cyclic unsaturated aliphatic polyvalent amine, but is preferably an acyclic saturated aliphatic polyvalent amine. The polyvalent amine may be the same as a biological component or a derivative thereof. For example, the polyvalent amine may be a basic amino acid or a derivative thereof.

In the present invention, the polyvalent amine may be, for example, a substituted or unsubstituted, aliphatic polyvalent amine or aromatic polyvalent amine optionally having a heteroatom in the main chain.

In the present invention, examples of the substituent include an alkyl group, an aminoalkyl group, a hydroxyalkyl group, an alkyl ester group, an alkoxy group, an amino group, a formyl group, a hydroxy group, a carboxy group, and a carbonyl group. When the substituent contains a reactive functional group (e.g., an aminoalkyl group), the substituent does not form the main chain of the polyvalent amine. The substituent is preferably an alkyl group, an aminoalkyl group, an alkyl ester group, or a hydroxy group. The alkyl group, the aminoalkyl group, the hydroxyalkyl group, the alkyl ester group, and the alkoxy group each preferably have one to five carbon atoms, more preferably one to three carbon atoms. The alkyl group is preferably a C1 to C3 alkyl group; i.e., a methyl group, an ethyl group, or a propyl group. The aminoalkyl group is preferably an aminomethyl group, an aminoethyl group, or an aminopropyl group. Examples of the alkyl ester group include a methyl ester group, an ethyl ester group, a propyl ester group, and a butyl ester group. Of these, preferred is a methyl ester group or an ethyl ester group. The polyvalent amine may have any number of substituents. The polyvalent amine may have one to five substituents at substitutable positions. The polyvalent amine preferably has one to three substituents. If the polyvalent amine has two or more substituents, the substituents may be identical to or different from one another.

In the present invention, examples of the heteroatom include nitrogen, oxygen, and sulfur. The polyvalent amine may have any number of heteroatoms in the main chain. The polyvalent amine has, for example, one to five heteroatoms or one to three heteroatoms. When the polyvalent amine has two or more heteroatoms, the heteroatoms may be identical to or different from one another. When the polyvalent amine has two or more heteroatoms in the main chain, these heteroatoms may be located separately so as to prevent direct bonding therebetween. When the polyvalent amine has a heteroatom in the main chain, the heteroatom may be located at a position other than a position where a reactive functional group (in particular, a primary amino group) is directly bonded.

In the present invention, the number of carbon atoms in the main chain of the polyvalent amine is, for example, 1 or more, or 2 or more, and is, for example, 20 or less, 12 or less, 10 or less, 8 or less, 6 or less, or 4 or less. The number of carbon atoms is, for example, 1 to 20, 1 to 12, 1 to 10, 1 to 8, 1 to 6, 1 to 4, 2 to 20, 2 to 12, 2 to 10, 2 to 8, 2 to 6, 2 to 4, 1, 2, 3, 4, 5, 6, 7, 8, 9, 10, 11, or 12. The number of carbon atoms in the main chain of the polyvalent amine is preferably 1 to 10, more preferably 1 to 8, still more preferably 1 to 6, particularly preferably 2 to 4, from a viewpoint of an improvement in cross-linking efficiency. The number of carbon atoms in the main chain of the polyvalent amine is preferably 1 to 10, more preferably 1 to 8, still more preferably 1 to 6, yet more preferably 2 to 5, yet still more preferably 2 to 4, from a viewpoint of an improvement in medical efficacy.

In the present invention, the number of atoms in the main chain of the polyvalent amine is, for example, 1 or more, or 2 or more, and is, for example, 20 or less, 12 or less, 11 or less, 10 or less, 8 or less, 6 or less, or 4 or less. The number of atoms is, for example, 1 to 20, 1 to 12, 1 to 11, 1 to 10, 1 to 8, 1 to 6, 1 to 4, 2 to 20, 2 to 12, 2 to 11, 2 to 10, 2 to 8, 2 to 6, 2 to 4, 1, 2, 3, 4, 5, 6, 7, 8, 9, 10, 11, or 12. The number of atoms in the main chain of the polyvalent amine is preferably 1 to 11, more preferably 1 to 10, still more preferably 1 to 8, yet more preferably 1 to 6, particularly preferably 2 to 4, from a viewpoint of an improvement in cross-linking efficiency. The number of atoms in the main chain of the polyvalent amine is preferably 1 to 11, more preferably 1 to 10, still more preferably 1 to 8, yet more preferably 1 to 6, yet still more preferably 2 to 5, particularly preferably 2 to 4, from a viewpoint of an improvement in medical efficacy.

In the present invention, the polyvalent amine is preferably a triamine or a diamine, and more preferably a diamine.

In the present invention, the polyvalent amine is preferably an aliphatic diamine or an aromatic diamine, and more preferably an aliphatic diamine. The aliphatic diamine may be, for example, an acyclic aliphatic diamine or a cyclic aliphatic diamine, but is preferably an acyclic aliphatic diamine. Examples of the cyclic aliphatic diamine include a cycloalkylenediamine and a bis(aminoalkyl)cycloalkane. Examples of the acyclic aliphatic diamine include an alkylenediamine, an alkenylenediamine, and an alkynylenediamine. Of these, an alkylenediamine and an alkenylenediamine are preferred, and an alkylenediamine is particularly preferred. Examples of the aromatic diamine include an arylenediamine and a bis(aminoalkyl)benzene.

In the present invention, specific examples of the polyvalent amine include an alkylenediamine, such as ethane-1, 2-diamine, 1,3-diaminopropane, 1,4-diaminobutane (putrescine), 1,5-diaminopentane (cadaverine), 1,6-diaminohexane, 1,7-diaminoheptane, 1,8-diaminooctane, 1,9-diaminononane, 1,10-diaminodecane, 1,11-diaminoundecane, 1,12-diaminododecane, 1,3-diamino-2-propanol, 2,2'-thiodiethanamine, 2,2'-oxydiethanamine, 1,11-diamino-3,6,9-trioxaundecane, L-lysine ethyl ester, L-ornithine ethyl ester, N-(2-aminoethyl)-1,2-ethanediamine, N-(3-aminopropyl)butane-1,4-diamine (spermidine), and N,N'-bis(3-aminopropyl)butane-1,4-diamine (spermine); triamines, such as propane-1,2,3-triamine, pentane-1,3,5-triamine, and 2-(aminomethyl)-2-methylpropane-1,3-diamine; 1,4-bis(aminomethyl)cyclohexane; 1,4-bis(aminomethyl)benzene; (E)-2-butene-1,4-diamine; and a salt form thereof. These amines may be used singly or in combination of two or more species.

In the present invention, no particular limitation is imposed on the polyvalent epoxy compound, so long as it has two or more epoxy groups. Examples of the diepoxy compound include a diglycidyl compound.

In the present invention, no particular limitation is imposed on the polyvalent vinyl compound, so long as it has two or more vinyl groups. Examples of the divinyl compound include a divinyl sulfone.

In the present invention, examples of the epihalohydrin include an epichlorohydrin.

<Cross-Linked Structure>

As used herein, the term "cross-linked structure" refers to a structure formed within a single CS molecule or between different CS molecules through covalent bonding with a cross-linker.

When the cross-linker is a polyvalent amine, the cross-linked CS of the present invention may have a cross-linked structure represented by the following formula (I):

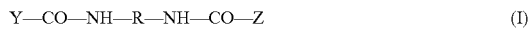

Y—CO—NH—R—NH—CO—Z  (I)

(where Y—CO— represents a disaccharide unit moiety in a chondroitin sulfate molecule;

—CO—Z represents a disaccharide unit moiety in the same chondroitin sulfate molecule or a different chondroitin sulfate molecule;

R represents a substituted or unsubstituted hydrocarbon group optionally having a heteroatom in the main chain; and —CO—NH— and —NH—CO— each represent an amide bond formed between an amino group of a polyvalent amine and a carboxy group of a glucuronic acid, which is a constitutive sugar moiety in chondroitin sulfate).

When the cross-linker is a polyvalent amine, the cross-linked CS of the present invention may have a structure represented by the following formula (III):

Y—CO—NH—R—NH$_2$  (III)

(where Y—CO—, R, and —CO—NH— each represent the same embodiments as defined in the formula (I) above). That is, the cross-linked CS of the present invention may have a structure in which one amino group of the polyvalent amine is covalently bonded to CS.

In the formula (I) or (III), —NH—R—NH— or —NH—R—NH$_2$ is a group in a polyvalent amine. Thus, the description, examples, and preferred ranges regarding the polyvalent amine in the present invention described above in the section <cross-linker> can be applied mutatis mutandis to those.

R in the formulae (I) and (III) may be a substituted or unsubstituted hydrocarbon group optionally having a heteroatom in the main chain. The hydrocarbon group may be an aliphatic hydrocarbon group or an aromatic hydrocarbon group, but is preferably an aliphatic hydrocarbon group. The aliphatic hydrocarbon group may be an acyclic aliphatic hydrocarbon group or a cyclic aliphatic hydrocarbon group, but is preferably an acyclic aliphatic hydrocarbon group. The aliphatic hydrocarbon group may be a saturated aliphatic hydrocarbon group or an unsaturated aliphatic hydrocarbon group. That is, the aliphatic hydrocarbon group may be an acyclic saturated aliphatic hydrocarbon group, an acyclic unsaturated aliphatic hydrocarbon group, a cyclic saturated aliphatic hydrocarbon group, or a cyclic unsaturated aliphatic hydrocarbon group, but is preferably an acyclic saturated aliphatic hydrocarbon group. Examples of the acyclic aliphatic hydrocarbon group include an alkylene group, an alkenylene group, and an alkynylene group. Of these, an alkylene group or an alkenylene group is preferred, and an alkylene group is more preferred. Examples of the cyclic aliphatic hydrocarbon group include a cycloalkylene group and a cycloalkylalkylene group. Examples of the aromatic hydrocarbon group include an arylene group and an arylalkylene group. R in the formulae (I) and (III) may be a hydrocarbon group other than an unsubstituted hydrocarbon group having no heteroatom in the main chain.

The description, examples, and preferred ranges regarding the polyvalent amine in the present invention described above in the section <cross-linker> can be applied mutatis mutandis to the substituent and heteroatom in the present invention.

R in the formulae (I) and (III) may be a hydrocarbon group having no biodegradable moiety. Alternatively, R may be a hydrocarbon group having no biodegradable moiety in the main chain. The biodegradable moiety may be, for example, an ester bond or a thioester bond. Thus, R may be a hydrocarbon group having neither an ester bond nor a thioester bond in the main chain.

R in the formulae (I) and (III) may be a hydrocarbon group having no disulfide bond. Alternatively, R may be a hydrocarbon group having no disulfide bond in the main chain. When R has two or more heteroatoms in the main chain, these heteroatoms may be located so as to prevent direct bonding therebetween. In the formulae (I) and (III), the terminal atoms of R bonded to the nitrogen atoms may be carbon atoms.

The description, examples, and preferred ranges regarding the number of carbon atoms and atoms in the main chain of the polyvalent amine in the present invention described above in the section <cross-linker> can be applied mutatis mutandis to the number of carbon atoms and atoms in the main chain of R in the formulae (I) and (III).

In one embodiment of the cross-linked CS of the present invention, R in the formulae (I) and (III) is —CH$_2$CH$_2$—(R$^1$—CH$_2$CH$_2$)$_n$— (where R$^1$ represents an oxygen atom, a sulfur atom, or —NH; when n is 2 or more, the radicals R$^1$ may be identical to or different from one another; and n represents an integer of 1 to 5 or 1 to 3).

In one embodiment of the cross-linked CS of the present invention, R in the formulae (I) and (III) is —(CH$_2$)$_l$—(CR$^2$R$^3$)—(CH$_2$)$_m$— (where R$^2$ and R$^3$ each independently represent a hydrogen atom, —OH, —NH$_2$, or a C1 to C3 alkyl group, alkyl ester group, or aminoalkyl group; l represents an integer of 1 to 5; and m represents an integer of 0 to 5). In a further embodiment, R is —(CH$_2$)$_l$—(CR$^2$R$^3$)—(CH$_2$)$_m$— (where R$^2$, R$^3$, l, and m are the same as defined above; and when R$^2$ is hydrogen atom, R$^3$ is not a hydrogen atom). In another further embodiment, R is —(CH$_2$)$_l$—(CR$^2$R$^3$)—(CH$_2$)$_m$— (where R$^2$, R$^3$, and l are the same as defined above; m represents an integer of 1 to 5; and when $R^2$ is hydrogen atom, $R^3$ is not a hydrogen atom).

In one embodiment of the cross-linked CS of the present invention, R in the formulae (I) and (III) is —$(CH_2)_p$—CH=CH—$(CH_2)_q$— (where p and q each independently represent an integer of 0 to 3 or 1 to 2).

Specific examples of R in the formulae (I) and (III) include —$(CH_2)_2$—, —$(CH_2)_3$—, —$(CH_2)_4$—, —$(CH_2)_5$—, —$(CH_2)_6$—, —$(CH_2)_7$—, —$(CH_2)_8$—, —$(CH_2)_9$—, —$(CH_2)_{10}$—, —$(CH_2)_{11}$—, —$(CH_2)_{12}$—, —$CH_2CH=CHCH_2$—, —$CH_2CH(OH)CH_2$—, —$CH_2CH_2$—S—$CH_2CH_2$—, —$CH_2CH_2$—O—$CH_2CH_2$—, —$CH_2CH_2O$—$CH_2CH_2$—$CH_2CH_2$—$CH_2CH_2$—, $CH_2CH(NH_2)CH_2$—, —$CH_2CH_2CH(NH_2)$—$CH_2CH_2$—, —$CH_2CH_2$—NH—$CH_2CH_2$—, —$CH_2$—X—$CH_2$—, —$CH_2$-Ph-$CH_2$—, —$CH_2C(CH_2NH_2)(CH_3)$—$CH_2$—, —$(CH_2)_4$—NH—$(CH_2)_3$—, —$(CH_2)_3$—NH—$(CH_2)_4$—NH—$(CH_2)_3$—, —$(CH_2)_4$—CH(COOCH_2CH_3)$—, and —$(CH_2)_3$—CH(COOCH_2CH_3)$— (where X represents a 1,4-cyclohexylene group, and Ph represents a 1,4-phenylene group).

If the cross-linker is a polyvalent amine, all the carboxy groups in CS do not necessarily form amide bonds with the cross-linker; i.e., some of the carboxy groups may form amide bonds with the cross-linker.

One embodiment of the cross-linked CS of the present invention is as follows.

A CS derivative having a cross-linked structure formed with a group in a polyvalent amine, the cross-linked structure being present between disaccharide units of CS, wherein the cross-linked structure is represented by the following formula (I):

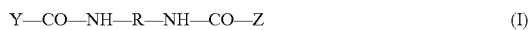

Y—CO—NH—R—NH—CO—Z                    (I)

(where Y—CO— represents a disaccharide unit moiety in a CS molecule;

—CO—Z represents a disaccharide unit moiety in the same CS molecule or a different CS molecule;

R represents a substituted or unsubstituted aliphatic hydrocarbon group having 1 to 11 atoms in the main chain and optionally having a heteroatom in the main chain, the heteroatom is one to three atoms selected from the group consisting of nitrogen, oxygen, and sulfur, and the substituted hydrocarbon group has at least one substituent selected from the group consisting of a C1 to C3 alkyl group, a C1 to C3 aminoalkyl group, a C1 to C3 hydroxyalkyl group, a C1 to C3 alkyl ester group, a C1 to C3 alkoxy group, an amino group, a formyl group, a hydroxy group, and a carboxy group; and —CO—NH— and —NH—CO— each represent an amide bond formed between an amino group of a polyvalent amine and the carboxy group of glucuronic acid, which is a constitutive sugar of CS). In the cross-linked CS according to this embodiment, R in the formula (I) may be a hydrocarbon group that does not have a biodegradable moiety and/or a disulfide bond in the main chain.

<Method for Producing Cross-Linked CS>

The cross-linked CS of the present invention can be produced through covalent bonding of two functional groups of CS and two reactive functional groups of a cross-linking agent by a common process. The two functional groups of CS may be present in a single CS molecule or in different CS molecules. The cross-linking agent may be a polyfunctional cross-linking agent, such as a polyvalent amine, a polyvalent epoxy compound, a polyvalent vinyl compound, or an epihalohydrin. The examples and preferred ranges described above in the section <cross-linker> can be applied mutatis mutandis to the linking agent.

The concentration of CS in a solvent used for the cross-linking reaction between CS and the cross-linking agent is preferably 2 to 20% by weight (hereinafter may be referred to as "wt. %"), more preferably 2 to 15 wt. %, particularly preferably 3 to 15 wt. %.

No particular limitation is imposed on the solvent used for cross-linking reaction, so long as it dissolves CS and the cross-linking agent. The solvent is preferably water or a mixture of water and a water-miscible organic solvent. Examples of the water-miscible organic solvent include, but are not particularly limited to, lower alcohols, such as methanol, ethanol, isopropanol, n-propanol, and tertiary butanol; glycol ethers, such as ethylene glycol monomethyl ether and ethylene glycol monoethyl ether; acetone; 1,4-dioxane; tetrahydrofuran; and acetonitrile. Of these, methanol, ethanol, acetone, tetrahydrofuran, and 1,4-dioxane are preferred. These water-miscible organic solvents, which are mixed with water, may be used singly or in combination of two or more species.

No particular limitation is imposed on the reaction time of cross-linking. The reaction time of cross-linking may be, for example, 1 to 48 hours, 1 to 24 hours, 2 to 20 hours, or overnight. As used herein, the term "overnight" refers to 10 to 24 hours. The cross-linking reaction may be stopped during the reaction by, for example, addition of 10% aqueous sodium carbonate solution. No particular limitation is imposed on the reaction temperature of cross-linking. The reaction temperature of cross-linking, which is appropriately determined depending on the type of the solvent used, is preferably 5 to 60° C., more preferably 15 to 30° C.

The cross-linking reaction may be appropriately followed by an alkali treatment step. No particular limitation is imposed on the alkali treatment for alkalifying the reaction mixture obtained through the cross-linking reaction, so long as the treated reaction mixture exhibits alkalinity. Specifically, the alkali treatment preferably involves the use of an inorganic base. In particular, sodium hydroxide, sodium hydrogen carbonate, or sodium carbonate is preferably used. The alkali treatment is performed at a pH of, for example, 7.2 to 11, preferably at a pH of 7.5 to 10. No particular limitation is imposed on the time of alkali treatment. The time of alkali treatment is, for example, 2 to 12 hours, preferably 2 to 6 hours. The temperature of alkali treatment is preferably 5 to 60° C., more preferably 15 to 30° C.

After the cross-linking reaction or the alkali treatment step, the reaction mixture containing cross-linked CS is subjected to 1) an agitation step, 2) a precipitation step, 3) a washing step, and 4) a drying step, thereby finally preparing a dry powder of cross-linked CS.

The agitation step, the precipitation step, the washing step, and the drying step may be carried out by a method generally known to those skilled in the art. No particular limitation is imposed on the method.

<Cross-Linking of CS Using Polyvalent Amine as Cross-Linking Agent>

When a polyvalent amine is used as a cross-linking agent, CS can be cross-linked through covalent bonding between a carboxy group of CS and an amino group of the cross-linking agent by a common amidation method.

In this case, the amidation method may be, for example a method using, in a solvent, a condensing agent, such as a water-soluble carbodiimide (e.g., 1-ethyl-3-(3-dimethylaminopropyl)carbodiimide), dicyclohexylcarbodiimide (DCC), or 4-(4,6-dimethoxy-1,3,5-triazin-2-yl)-4-methylmorpholinium chloride N hydrate (DMT-MM); the symmetric acid anhydride method; the mixed acid anhydride method; or the active ester method. The reaction conditions for the amidation method are appropriately determined depending on the CS and cross-linking agent used.

In the case of the cross-linking reaction between a carboxy group of CS and a polyvalent amine as a cross-linking agent, the concentration of CS in a solvent is preferably 2 to 20 wt. %, more preferably 2 to 15 wt. %, particularly preferably 3 to 15 wt. %.

The mole equivalent (eq) of the polyvalent amine as a cross-linking agent is preferably 0.005 to 0.500 eq, more preferably 0.005 to 0.300 eq, still more preferably 0.005 to 0.250 eq, yet more preferably 0.005 to 0.200 eq, particularly preferably 0.005 to 0.100 eq, relative to 1.00 mole equivalent (eq) of the disaccharide unit of CS.

The mole equivalent (eq) of the condensing agent is preferably [(0.50 to 5.00)×valence] eq, more preferably [(1.00 to 4.00)×valence] eq, particularly preferably [(1.00 to 3.00)×valence] eq, relative to 1.00 mole equivalent (eq) of the polyvalent amine as a cross-linking agent. As used herein, the term "valence" refers to the valence of the polyvalent amine.

The examples and preferred ranges described above can be applied mutatis mutandis to the solvent used for the cross-linking reaction, the reaction time of cross-linking, and the reaction temperature of cross-linking. The amidation method used for the cross-linking reaction, the CS concentration, the structure of the polyvalent amine as a cross-linking agent, the amount of the cross-linking agent added, the amount of the condensing agent added, and the solvent are appropriately determined depending on the properties required for the cross-linked CS.

In the case of cross-linking by use of a hydroxy group of CS, cross-linked CS products having a variety of structures may be produced depending on the cross-linked position of the hydroxy groups. Thus, the cross-linking by use of a carboxy group of CS is preferably selected for reducing the structural diversity of the cross-linked CS. The cross-linking agent is preferably a polyvalent amine in view of formation of an amide bond between the polyvalent amine and a carboxy group of CS. In order to reduce the structural diversity of the cross-linked CS, a diamine is particularly preferred.

The cross-linked structure of the cross-linked CS can be determined by, for example, the method described in Example 12A.

<Percent of Cross-Linking>

As used herein, the percent of cross-linking of the cross-linked CS refers to the percentage of the number of cross-linkers (wherein two or more functional groups are bonded to CS) relative to the number of disaccharide units of CS. For example, the percent of cross-linking of a CS derivative having a cross-linked structure formed with a group in a diamine is calculated by the following formula (A):

[Formula 1]

(the amount by mole (mol) of a cross-linker wherein
both terminal amino groups are bonded to CS)/
(the total amount by mole (mol) of —COR in
the cross-linked CS)×100(%)    (A)

(where R represents —OH, —OM (M represents a metal of group 1 or 2 of the periodic table), or a group in a diamine).

No particular limitation is imposed on the percent of cross-linking of the cross-linked CS of the present invention. The percent of cross-linking may be, for example, 0.01% or more, 0.05% or more, 0.1% or more, 0.5% or more, 30% or less, 10% or less, 5% or less, 3% or less, or 1% or less. The percent of cross-linking is preferably 0.01 to 30%, more preferably 0.05 to 10%, still more preferably 0.1 to 5%, yet more preferably 0.25 to 4%, particularly preferably 0.5 to 3%.

<Determination of Percent of Cross-Linking>

The percent of cross-linking of the CS derivative having a cross-linked structure through a group in a diamine can be determined by, for example, the method described below. Specifically, dilute sulfuric acid is added to a test substance followed by being heated at 60° C. for six hours, and the resultant solution is then basified. Propylene oxide is added to the basified solution and heated at 60° C. overnight. The strongly acidified solution is heated at 110° C. overnight, and the resultant solution is basified. The amino group of the cross-linker is labeled with phenyl isothiocyanate, and the labeled cross-linker is quantified by means of LC/MS. The ratio of the amount by mole of the cross-linker to that of the disaccharide unit of CS is calculated in percentage.

<Pharmaceutically Acceptable Carrier>

Example of the "pharmaceutically acceptable carrier" as used herein include saline, phosphate buffered saline, purified water, and water for injection. The pharmaceutically acceptable carrier may contain a common additive, such as a pH adjuster, a buffer, an isotonizing agent, a stabilizer, or a preservative. Examples of the additive include sodium chloride, potassium chloride, sodium dihydrogen phosphate, disodium hydrogen phosphate, monopotassium dihydrogen phosphate, sodium edetate, and benzalkonium chloride.

<Composition Containing Cross-Linked CS>

No particular limitation is imposed on the method for preparing the composition containing the cross-linked CS of the present invention (hereinafter may be referred to as "the composition of the present invention"). For example, the composition of the present invention can be prepared by mixing the cross-linked CS of the present invention with a pharmaceutically acceptable carrier, and shaking the resultant mixture by means of a shaking apparatus for 4 to 24 hours or longer.

The composition containing the cross-linked CS of the present invention is preferably in the form of a liquid, more preferably in the form of an aqueous solution in view of sufficiently homogeneous dispersion of the microparticulate solute in a solvent. As used herein, the term "aqueous solution" refers to a composition containing water as a solvent and being in a clear form (hereinafter may be referred to as "solution form"). The solution form can be determined by the "test for determining solution form" described below. In the case where the composition of the present invention is used as a pharmaceutical preparation (e.g., an eye drop), the presence of insoluble matter in the composition may cause a foreign body. Thus, the composition of the present invention is preferably in the form of an aqueous solution. The composition containing water as a solvent is, for example, a composition prepared by mixing the cross-linked CS of the present invention with saline, phosphate buffered saline, purified water, or water for injection.

The cross-linked CS of the present invention is preferably water-soluble. The "test for determining water solubility" described below can determine whether or not the cross-linked CS is water-soluble.

In the composition containing the cross-linked CS of the present invention, the cross-linked CS exhibits a filter-passing rate of preferably 50% or more, more preferably 60% or more, still more preferably 70% or more, yet more preferably 80% or more, particularly preferably 85% or more.

The composition containing the cross-linked CS of the present invention may have a viscosity of 5 to 11,000, 10 to 5,000, 20 to 1,000, 30 to 300, or 30 to 250 mPa·s. The concentration of the cross-linked CS in the composition containing the cross-linked CS of the present invention may be 0.1 to 15 wt. %, 0.3 to 13 wt. %, or 1 to 10 wt. % relative to the entire amount of the composition.

<Test for Determining Solution Form>

The absorbance of a prepared composition at 600 nm is measured by means of an ultraviolet visible spectrophotometer (UV-1800, manufactured by Shimadzu Corporation). A composition exhibiting an absorbance of 0.1 or less is determined as "clear," and a composition exhibiting an absorbance of more than 0.1 is determined as "turbid."

<Test for Determining Water Solubility>

A cross-linked CS is dissolved in water or PBS so as to achieve a concentration of 2.0% (w/w), and the absorbance of the resultant composition at 600 nm is measured by means of an ultraviolet visible spectrophotometer (UV-1800, manufactured by Shimadzu Corporation). A cross-linked CS exhibiting an absorbance of 0.1 or less is determined as "water-soluble."

<Measurement of Viscosity>

The viscosity of the composition is measured at 25° C. and 5 rpm by means of an E-type rotary viscometer (TV-L/H, Toki Sangyo Co., Ltd.) with a standard cone (CORD-1, 1°34'×R24). The measured viscosity is defined as "viscosity" (mPa·s) as used herein. If the viscosity at 5 rpm falls outside the range of detection, an extrapolated value is determined at another rotation speed, and the value is defined as "viscosity" (mPa·s) as used herein.

<Test for Filter-Passing Rate>

A sample is passed through a porous filter (pore size: 5.0 μm, diameter: 25 mm) at 25° C., and the CS concentration (in terms of disaccharide unit) of the sample (hereinafter may be referred to as "CS concentration") is measured before and after the passage of the sample through the filter by the carbazole-sulfuric acid method described below. The "filter-passing rate" as used herein is calculated by the following formula (B). The pressure during passage of the sample through the filter is adjusted to 5.3 kgf/cm² or less.

[Formula 2]

$$(\text{the CS concentration (wt. \%) of a sample after passage through a filter})/(\text{the CS concentration (wt. \%) of the sample before passage through the filter}) \times 100 (\%) \quad (B)$$

For example, when the CS concentration of a sample before passage through a filter is 1.00% and the CS concentration of the sample after passage through the filter is 0.90%, the filter-passing rate is 90%.

<Calculation of CS Concentration by the Carbazole-Sulfuric Acid Method>

The CS concentration (mol/L) is calculated by the following formula (C) in accordance with the carbazole-sulfuric acid method by use of 20.0 μg/mL aqueous D-glucuronolactone (molecular weight: 176.12) solution as a standard.

[Formula 3]

$$\text{OD530 [sample]} \div \text{OD530 [standard]} \times \text{D-glucuronolactone concentration (mol/L)} \quad (C)$$

(where OD530 corresponds to optical density at a wavelength of 530 nm).

The cross-linked CS of the present invention and the composition of the present invention can be used, for example, as a pharmaceutical preparation or an agent for the treatment of an eye disease. Thus, the cross-linked CS of the present invention can be used as an active pharmaceutical ingredient of a pharmaceutical preparation or an agent for the treatment of an eye disease.

<Agent for the Treatment of Eye Disease>

The agent for the treatment of an eye disease of the present invention contains the cross-linked CS of the present invention as an active pharmaceutical ingredient. The cross-linked CS is any of those described hereinabove; in particular, any of the aforementioned CS derivatives according to embodiments [A1] to [A22]. No particular limitation is imposed on the "eye disease" as used herein, so long as it causes any abnormality in the anterior segment of the eye. The anterior segment of the eye is preferably the ocular surface, more preferably the cornea, and particularly preferably the superficial cornea. The "anterior segment of the eye" as used herein includes tear. The "eye disease" as used herein is preferably corneal epithelial disorder, abnormal tear film, or dry eye, and particularly preferably corneal epithelial disorder or dry eye. The "dry eye" as used herein may be either or both of dry eye disease and dry eye syndrome. The term "abnormal tear film" corresponds to the state where the tear film is broken or the tear film is likely to be broken, and includes the state of "tear film instability" according to the definition of dry eye by DEWS (The Ocular Surface Vol. 5, No. 2: 75-92, 2007). Abnormal tear film is caused by, for example, increased tear evaporation or reduced tear volume. Abnormal tear film can be determined by, for example, the Schirmer test, breakup time (BUT), or surface regularity index (SRI).

No particular limitation is imposed on the "corneal epithelial disorder," so long as it is the disorder in superficial cornea. The corneal epithelial disorder is, for example, corneal epithelial defect, corneal erosion, corneal ulcer, corneal perforation. Examples of the corneal epithelial disorder include corneal epithelial disorders caused by superficial punctate keratopathy, keratitis, or the like. Other examples of the corneal epithelial disorder include corneal epithelial disorders caused by endogenous diseases, such as dry eye, Sjogren's syndrome, and Stevens-Johnson syndrome; and corneal epithelial disorders caused by exogenous factors, such as contact lens wear, trauma, surgery, infection, or pharmaceutical preparation. Particularly preferred is a corneal epithelial disorder caused by dry eye.

The term "treatment" as used herein includes therapy. The term "therapy" includes amelioration, healing, and healing acceleration. Thus, the term "agent for the treatment" includes a therapeutic agent, and the term "therapeutic agent" includes an ameliorating agent and a healing accelerator. As used herein, the therapy for abnormal tear film may be referred to as "tear film stabilization."

The "agent for the treatment of eye disease" as used herein is preferably an agent for the treatment of abnormality in the anterior segment of the eye, in particular, abnormality in the ocular surface or tear. Specific examples of the agent include an agent for the treatment of a corneal epithelial disorder, a tear film stabilizer, and an agent for the treatment of dry eye.

<Dosage Form and Preparation>

No particular limitation is imposed on the dosage form of the agent for the treatment of an eye disease containing the cross-linked CS of the present invention as an active pharmaceutical ingredient (hereinafter the agent may be referred to as "the agent of the present invention"). Examples of the dosage form include an eye drop, an eye ointment, a cream, and a lotion. Of these, an eye drop is preferred, and an aqueous eye drop is particularly preferred. The term "aqueous eye drop" refers to an eye drop containing water in an amount of 50 wt. % or more. The aqueous eye drop of the present invention contains water in an amount of preferably 80 wt. % or more, more preferably 90 wt. % or more. The aqueous eye drop of the present invention may contain any pharmaceutically or physiologically acceptable water. Examples of the water include distilled water, purified water, sterilized purified water, water for injection, and distilled water for injection. These definitions are based on The Japanese Pharmacopoeia, Sixteenth Edition. The eye drop may contain, for example, saline or phosphate buffered saline. The eye drop may appropriately contain a common additive, such as a pH adjuster, a buffer, an isotonizing agent, a stabilizer, or a preservative. Examples of the additive include sodium chloride, potassium chloride, sodium dihydrogen phosphate, disodium hydrogen phosphate, monopotassium dihydrogen phosphate, sodium edetate, and benzalkonium chloride. No particular limitation is imposed on the pH and osmotic pressure ratio of the eye drop, so long as they fall within ranges acceptable for ophthalmic preparations. The agent of the present invention does not necessarily contain hyaluronic acid.

The agent of the present invention is preferably in the form of a liquid, more preferably in the form of an aqueous solution in view of sufficiently homogeneous dispersion of the microparticulate solute in a solvent. In the case where the agent of the present invention is used as an eye drop, the presence of insoluble matter in the agent may cause a foreign body sensation. Thus, the agent of the present invention is preferably in the form of an aqueous solution. In the agent of the present invention, the cross-linked CS exhibits a filter-passing rate of preferably 60% or more, more preferably 70% or more, still more preferably 80% or more, particularly preferably 85% or more.

No particular limitation is imposed on the concentration of the cross-linked CS in the agent of the present invention, so long as it is an effective concentration exhibiting a desired medical efficacy. The concentration of the cross-linked CS is, for example, 0.01 to 20 wt. %, 0.1 to 15 wt. %, or 0.3 to 10 wt. %.

<Application Target>

The application target of the agent of the present invention is preferably a mammal. Examples of the mammal include, but are not particularly limited to, human, equine, bovine, canine, feline, rabbit, hamster, guinea pig, and mouse. The agent of the present invention can serve as a pharmaceutical preparation for a human or an animal, preferably a pharmaceutical preparation for a human <Usage and Dosage>

The dosage of the agent of the present invention can be appropriately varied depending on, for example, the degree of patient's symptom, the age or body weight of a patient, or the diagnosis by a physician.

No particular limitation is imposed on the number of instillation times of the agent of the present invention per day or the instillation period. The number of instillation times of the agent per day is, for example, one to eight, one to six, one to four, one to three, one, or two, and the number may be "appropriately increased or decreased. No particular limitation is imposed on the instillation period, and the period is, for example, one week to several months. The agent is preferably instilled every day. For the case of an eye drop, for example, one or two drops or one to three drops are instilled with single application; specifically, one to eight ocular instillations per day (one to three drops per instillation), one to six ocular instillations per day (one to three drops per instillation), one to four ocular instillations per day (one to three drops per instillation), one to three ocular instillations per day (one to three drops per instillation), or one or two ocular instillations per day (one to three drops per instillation). For example, the eye drop is instilled every day.

<Method of Using the Agent of the Present Invention>

The agent of the present invention can be instilled into the eyes of a human or an animal. No particular limitation is imposed on the instillation of the agent of the present invention into the eye(s) of a human or an animal, so long as the agent is instilled in a medically acceptable manner so that the advantageous effects of the present invention are achieved.

No particular limitation is imposed on the specific manner of instillation of the agent. The installation manner may be appropriately determined depending on the form of dosage or preparation, and is preferably, for example, ocular instillation.

<Method for Treatment of Eye Disease>

The treatment method of the present invention is a method for the treatment of an eye disease, the method involving instillation of the agent of the present invention or the composition containing the cross-linked CS of the present invention into the eyes of a human or an animal. The treatment method of the present invention can be carried out in the same manner as described above, for example, in the sections <application target>, <usage and dosage>, and <method of using the agent of the present invention>.

EXAMPLES

The present invention will next be described in more detail by way of examples and test examples, which should not be construed as limiting the technical scope of the invention thereto. Unless otherwise specified, the "%" is on a mass basis. Unless otherwise specified, the mole equivalent (represented by "eq") of a polyvalent amine as a cross-linking agent and a condensing agent is relative to the disaccharide unit of CS.

Example 1

Production of Cross-Linked CS—NC2N
(A) Typical Example

CS (CSC, sodium chondroitin sulfate (Japanese Pharmaceutical Codex), weight average molecular weight: 40,000, Seikagaku Corporation) (2.00 g) (disaccharide unit: 3.91 mmol [calculated from the average molecular weight of the disaccharide unit (=511)], 1.00 eq) was dissolved in water for injection (WFI) so as to achieve a concentration of 10%. The resultant solution was mixed with ethanol (EtOH) (20.0 mL). A solution (4.00 mL) of ethane-1,2-diamine dihydrochloride (NC2N.2HCl, Wako Pure Chemical Industries, Ltd.) (i.e., a cross-linking agent) (10.4 mg, 0.0783 mmol, 0.0200 eq) in 50% ethanol and a solution (4.00 mL) of DMT-MM (TRIAZIMOCH, Tokuyama Corporation) (i.e., a condensing agent) (86.6 mg, 0.313 mmol, 0.0800 eq) in 50% ethanol were sequentially added dropwise to the mixture, and the resultant mixture was agitated at room temperature overnight (cross-linking reaction). 10% Aqueous sodium carbonate solution ($Na_2CO_3$/WFI) (20 mL) was added to the mixture, and the mixture was vigorously agitated for two to four hours. The resultant mixture was neutralized with 50 wt. % aqueous acetic acid solution (AcOH/WFI) (4.0 mL), and then sodium chloride (NaCl) (2.0 g) was added to the mixture, followed by precipitation with EtOH. The resultant precipitate was collected through filtration and washed with 90% EtOH (200 mL) thrice and then with EtOH (200 mL) twice. The resultant precipitate was dried under reduced pressure at 42° C. overnight, to thereby produce a cross-linked CS product (cross-linked CS—NC2N, compound 1) as a white powder (1.81 g).

(B) Production Example Different from Typical Example in Terms of Equivalent of Cross-Linking Agent The procedure of Example 1(A) was repeated, except that the mole equivalent of NC2N.2HCl was changed to 0.0050, 0.0100, 0.0150, 0.0175, 0.0225, 0.0250, and 0.0275 eq, and the mole equivalent of DMT-MM was changed to 0.0200, 0.0400, 0.0600, 0.0700, 0.0900, 0.100, and 0.110 eq, to thereby produce cross-linked CS products (cross-linked CS—NC2N, compounds 2 to 8) as white powders (about 1.75 g each).

Example 2

Production of Cross-Linked CS—NC2N (A) 10 g Scale

The procedure of Example 1(A) was repeated, except that the amount of CS was changed to 10 g, the mole equivalent of NC2N.2HCl was changed to 0.020 eq, and the mole equivalent of DMT-MM was changed to 0.080 eq, to thereby produce a cross-linked CS product (cross-linked CS—NC2N, compound 9) as a white powder (8.94 g).

(B) 20 g Scale

The procedure of Example 1(A) was repeated, except that the amount of CS was changed to 20 g, the mole equivalent of NC2N.2HCl was changed to 0.02375 eq, the mole equivalent of DMT-MM was changed to 0.0950 eq, and the reaction time of cross-linking was changed to 3 hours and 46 minutes, to thereby produce a cross-linked CS product (cross-linked CS—NC2N, compound 10) as a white powder (19.1 g).

Example 3

Production of Cross-Linked CS—NC3N

The procedure of Example 1(A) was repeated, except that the amount of CS was changed to 1 g, 1,3-diaminopropane dihydrochloride (NC3N.2HCl, Tokyo Chemical Industry Co., Ltd.) was used as a cross-linking agent (mole equivalent: 0.0150, 0.0200, 0.0300, and 0.0400 eq), and the mole equivalent of DMT-MM was changed to 0.0600, 0.0800, 0.120, and 0.160 eq, to thereby produce cross-linked CS products (cross-linked CS—NC3N, compounds 11 to 14) as white powders (about 0.84 g each).

Example 4

Production of Cross-Linked CS—NC4N

The procedure of Example 1(A) was repeated, except that the amount of CS was changed to 4 g, 1,4-diaminobutane dihydrochloride (NC4N.2HCl, Wako Pure Chemical Industries, Ltd.) was used as a cross-linking agent (mole equivalent: 0.0300, 0.0425, 0.0450, and 0.0475 eq), and the mole equivalent of DMT-MM was changed to 0.120, 0.170, 0.180, and 0.190 eq, to thereby produce cross-linked CS products (cross-linked CS—NC4N, compounds 15 to 18) as white powders (about 3.85 g each).

Example 5

Production of Cross-Linked CS—NC5N

The procedure of Example 1(A) was repeated, except that the amount of CS was changed to 1 g, 1,5-diaminopentane dihydrochloride (NC5N.2HCl, Tokyo Chemical Industry Co., Ltd.) was used as a cross-linking agent (mole equivalent: 0.0250, 0.0350, 0.0450, and 0.0550 eq), and the mole equivalent of DMT-MM was changed to 0.100, 0.140, 0.180, and 0.220 eq, to thereby produce cross-linked CS products (cross-linked CS—NC5N, compounds 19 to 22) as white powders (about 0.85 g each).

Example 6

Production of Cross-Linked CS—NC6N

The procedure of Example 1(A) was repeated, except that the amount of CS was changed to 4 g, 1,6-diaminohexane dihydrochloride (NC6N.2HCl, Wako Pure Chemical Industries, Ltd.) was used as a cross-linking agent (mole equivalent: 0.0400, 0.0525, 0.0550, and 0.0575 eq), and the mole equivalent of DMT-MM was changed to 0.160, 0.210, 0.220, and 0.230 eq, to thereby produce cross-linked CS products (cross-linked CS—NC6N, compounds 23 to 26) as white powders (about 3.83 g each).

Example 7

Production of Cross-Linked CS—NC8N

The procedure of Example 1(A) was repeated, except that the amount of CS was changed to 4 g, 1,8-diaminooctane dihydrochloride (NC8N.2HCl, prepared by addition of 1N hydrochloric acid (2.00 eq) to 1,8-diaminooctane [Wako Pure Chemical Industries, Ltd.]) was used as a cross-linking agent (mole equivalent: 0.0500, 0.0650, 0.0700, and 0.0725 eq), and the mole equivalent of DMT-MM was changed to 0.200, 0.260, 0.280, and 0.290 eq, to thereby produce cross-linked CS products (cross-linked CS—NC8N, compounds 27 to 30) as white powders (about 3.88 g each).

Example 8

Production of Cross-Linked CS—NC12N

The procedure of Example 1(A) was repeated, except that the amount of CS was changed to 1 g, 1,12-diaminododecane dihydrochloride (NC12N.2HCl, prepared by addition of 1N hydrochloric acid (2.00 eq) to 1,12-diaminododecane [Sigma-Aldrich]) was used as a cross-linking agent (mole equivalent: 0.0550 and 0.0700 eq), and the mole equivalent of DMT-MM was changed to 0.220 and 0.280 eq, to thereby produce cross-linked CS products (cross-linked CS—NC12N, compounds 31 and 32) as white powders (about 0.82 g each).

Example 9

Production of Cross-Linked CS-LysEt

The procedure of Example 1(A) was repeated, except that the amount of CS was changed to 1 g, L-lysine ethyl ester dihydrochloride (LysEt.2HCl, Sigma-Aldrich) was used as a cross-linking agent (mole equivalent: 0.0450 eq), the mole equivalent of DMT-MM was fixed to 0.180 eq, and the reaction time of cross-linking was changed to 2 hours, 3 hours, 3 hours and 40 minutes, 4 hours and 20 minutes, 5 hours, and 5 hours and 50 minutes, to thereby produce cross-linked CS products (cross-linked CS-LysEt, compounds 33 to 38) as white powders (about 1.04 g each).

Example 10

Production of Cross-Linked CS-OrnEt

The procedure of Example 1(A) was repeated, except that the amount of CS was changed to 2 g, ornithine ethyl ester dihydrochloride (OrnEt.2HCl, Chem-Impex International)

was used as a cross-linking agent (mole equivalent: 0.0200, 0.0300, 0.0325, and 0.0350 eq), and the mole equivalent of DMT-MM was changed to 0.0800, 0.120, 0.130, and 0.140 eq, to thereby produce cross-linked CS products (cross-linked CS-OrnEt, compounds 39 to 42) as white powders (about 1.99 g each).

Example 11

Production of Cross-Linked CS-Spermidine

The procedure of Example 1(A) was repeated, except that the amount of CS was changed to 1 or 2 g, spermidine trihydrochloride (Spermidine.3HCl, Sigma-Aldrich) was used as a cross-linking agent (mole equivalent: 0.0100, 0.0200, and 0.0220 eq), and the mole equivalent of DMT-MM was changed to 0.0400, 0.0800, and 0.0880 eq, to thereby produce cross-linked CS products (cross-linked CS-Spermidine, compounds 43, 44, and 67) as white powders (about 0.77 g, about 0.77 g, and about 1.75 g, respectively).

Example A1

Production of Cross-Linked CS-triAmine

The procedure of Example 1(A) was repeated, except that the amount of CS was changed to 2 g, 2-(aminomethyl)-2-methylpropane-1,3-diamine trihydrochloride (triAmine.3HCl, Aldrich) was used as a cross-linking agent (mole equivalent: 0.0091, 0.0092, and 0.0097 eq), and the mole equivalent of DMT-MM was changed to 0.0364, 0.0368, and 0.0388 eq, to thereby produce cross-linked CS products (cross-linked CS-triAmine, compounds 48 to 50) as white powders (about 1.74 g each).

Example A2

Production of Cross-Linked CS—NC3(OH)N

The procedure of Example 1(A) was repeated, except that the amount of CS was changed to 2 g, 1,3-diamino-2-propanol dihydrochloride (NC3(OH)N.2HCl, prepared by addition of 1N hydrochloric acid (2.00 eq) to 1,3-diamino-2-propanol [Aldrich]) was used as a cross-linking agent (mole equivalent: 0.0220, 0.0240, and 0.0260 eq), and the mole equivalent of DMT-MM was changed to 0.0880, 0.0960, and 0.1040 eq, to thereby produce cross-linked CS products (cross-linked CS—NC3(OH)N, compounds 51 to 53) as white powders (about 1.75 g each).

Example A3

Production of Cross-Linked CS—NC4(=)N

The procedure of Example 1(A) was repeated, except that the amount of CS was changed to 2 g, (E)-2-butene-1,4-diamine dihydrochloride (NC4(=)N.2HCl, Small Molecules, Inc.) was used as a cross-linking agent (mole equivalent: 0.0270 and 0.0275 eq), and the mole equivalent of DMT-MM was changed to 0.1080 and 0.1100 eq, to thereby produce cross-linked CS products (cross-linked CS—NC4(=)N, compounds 54 and 55) as white powders (about 1.80 g each).

Example A4

Production of Cross-Linked CS-Xylylene

The procedure of Example 1(A) was repeated, except that the amount of CS was changed to 2 g, 1,4-bis(aminomethyl)benzene dihydrochloride (Xylylene.2HCl, prepared by addition of 1N hydrochloric acid (2.00 eq) to 1,4-bis(aminomethyl)benzene [Aldrich]) was used as a cross-linking agent (mole equivalent: 0.0135, 0.0145, and 0.0150 eq), and the mole equivalent of DMT-MM was changed to 0.0540, 0.0580, and 0.0600 eq, to thereby produce cross-linked CS products (cross-linked CS-Xylylene, compounds 56 to 58) as white powders (about 1.77 g each).

Example A5

Production of Cross-Linked CS-Cyclohex

The procedure of Example 1(A) was repeated, except that the amount of CS was changed to 2 g, 1,4-bis(aminomethyl)cyclohexane dihydrochloride (Cyclohex.2HCl, prepared by addition of 1N hydrochloric acid (2.00 eq) to 1,4-bis(aminomethyl)cyclohexane [Kanto Chemical Co., Inc.]) was used as a cross-linking agent (mole equivalent: 0.0410 and 0.0425 eq), and the mole equivalent of DMT-MM was changed to 0.1640 and 0.1700 eq, to thereby produce cross-linked CS products (cross-linked CS-Cyclohex, compounds 59 and 60) as white powders (about 1.80 g each).

Example A6

Production of Cross-Linked CS—NC5(S)N

The procedure of Example 1(A) was repeated, except that the amount of CS was changed to 2 g, 2,2'-thiodiethanamine dihydrochloride (NC5(S)N.2HCl, prepared by addition of 1N hydrochloric acid (2.00 eq) to 2,2'-thiodiethanamine [Tokyo Chemical Industry Co., Ltd.]) was used as a cross-linking agent (mole equivalent: 0.0170 and 0.0180 eq), and the mole equivalent of DMT-MM was changed to 0.0680 and 0.0720 eq, to thereby produce cross-linked CS products (cross-linked CS—NC5(S)N, compounds 61 and 62) as white powders (about 1.77 g each).

Example A7

Production of Cross-Linked CS-Glycol(C5)

The procedure of Example 1(A) was repeated, except that the amount of CS was changed to 2 g, 2,2'-oxydiethanamine dihydrochloride (Glycol(C5).2HCl, Wako Pure Chemical Industries, Ltd.) was used as a cross-linking agent (mole equivalent: 0.0290 and 0.0310 eq), and the mole equivalent of DMT-MM was changed to 0.1160 and 0.1240 eq, to thereby produce cross-linked CS products (cross-linked CS-Glycol(C5), compounds 63 and 64) as white powders (about 1.76 g each).

Example A8

Production of Cross-Linked CS-Glycol(C11)

The procedure of Example 1(A) was repeated, except that the amount of CS was changed to 2 g, 1,11-diamino-3,6,9-trioxaundecane dihydrochloride (Glycol(C11).2HCl, prepared by addition of 1N hydrochloric acid (2.00 eq) to 1,11-diamino-3,6,9-trioxaundecane [Tokyo Chemical Industry Co., Ltd.]) was used as a cross-linking agent (mole equivalent: 0.0380 and 0.0410 eq), and the mole equivalent of DMT-MM was changed to 0.1520 and 0.1640 eq, to thereby produce cross-linked CS products (cross-linked CS-Glycol(C11), compounds 65 and 66) as white powders (about 1.87 g each).

Comparative Example 1

Production of CS—NC12N Derivative (Comparative Example)

A powder of a CS derivative modified with 1,12-diaminododecane was produced through the method described below. According to the literature from which the production method is cited, the modification is carried out for reducing the hydrophilicity of CS.

Through the method described in Example 5 "A. Modification of chondroitin" of WO 91/16881 and Biomaterials, 16: 473-478, 1995, CS derivatives ("CS—NC12N derivatives (Comparative Examples)," compounds 45 to 47) were produced as white powders (about 0.46 g each) by use of chondroitin sulfate A (CSA, Sigma-Aldrich) (1.00 g) (disaccharide unit: 2.18 mmol [calculated from the average molecular weight of the disaccharide unit (=458)], 1.00 eq), 1,12-diaminododecane dihydrochloride (Sigma-Aldrich) (mole equivalent: 0.30, 0.60, and 0.90 eq), and dicyclohexylcarbodiimide (DCC) serving as a condensing agent (mole equivalent: 0.66, 1.32, and 1.98 eq).

Tables 1 to 4 illustrate the compounds produced in the aforementioned Examples and Comparative Examples.

TABLE 1

| Compound | Cross-linked product | Cross-linking agent | Equivalent of cross-linking agent (eq) | Equivalent of DMT-MM (eq) |
|---|---|---|---|---|
| Compound 1 | Cross-linked CS-NC2N | NC2N•2HCl | 0.0200 | 0.0800 |
| Compound 2 | (Example 1, 2) | | 0.0050 | 0.0200 |
| Compound 3 | | | 0.0100 | 0.0400 |
| Compound 4 | | | 0.0150 | 0.0600 |
| Compound 5 | | | 0.0175 | 0.0700 |
| Compound 6 | | | 0.0225 | 0.0900 |
| Compound 7 | | | 0.0250 | 0.100 |
| Compound 8 | | | 0.0275 | 0.110 |
| Compound 9 | | | 0.020 | 0.080 |
| Compound 10 | | | 0.02375 | 0.0950 |
| Compound 11 | Cross-linked CS-NC3N | NC3N•2HCl | 0.0150 | 0.0600 |
| Compound 12 | (Example 3) | | 0.0200 | 0.0800 |
| Compound 13 | | | 0.0300 | 0.120 |
| Compound 14 | | | 0.0400 | 0.160 |
| Compound 15 | Cross-linked CS-NC4N | NC4N•2HCl | 0.0300 | 0.120 |
| Compound 16 | (Example 4) | | 0.0425 | 0.170 |
| Compound 17 | | | 0.0450 | 0.180 |
| Compound 18 | | | 0.0475 | 0.190 |
| Compound 19 | Cross-linked CS-NC5N | NC5N•2HCl | 0.0250 | 0.100 |
| Compound 20 | (Example 5) | | 0.0350 | 0.140 |
| Compound 21 | | | 0.0450 | 0.180 |
| Compound 22 | | | 0.0550 | 0.220 |
| Compound 23 | Cross-linked CS-NC6N | NC6N•2HCl | 0.0400 | 0.160 |
| Compound 24 | (Example 6) | | 0.0525 | 0.210 |
| Compound 25 | | | 0.0550 | 0.220 |
| Compound 26 | | | 0.0575 | 0.230 |
| Compound 27 | Cross-linked CS-NC8N | NC8N•2HCl | 0.0500 | 0.200 |
| Compound 28 | (Example 7) | | 0.0650 | 0.260 |
| Compound 29 | | | 0.0700 | 0.280 |
| Compound 30 | | | 0.0725 | 0.290 |
| Compound 31 | Cross-linked CS-NC12N | NC12N•2HCl | 0.0550 | 0.220 |
| Compound 32 | (Example 8) | | 0.0700 | 0.280 |

TABLE 2

| Compound | Cross-linked product | Cross-linking agent | Equivalent of cross-linking agent (eq) | Equivalent of DMT-MM (eq) |
|---|---|---|---|---|
| Compound 33[1] | Cross-linked CS-LysEt | LysEt•2HCl | 0.0450 | 0.180 |
| Compound 34[1] | (Example 9) | | | |
| Compound 35[1] | | | | |
| Compound 36[1] | | | | |
| Compound 37[1] | | | | |
| Compound 38[1] | | | | |
| Compound 39 | Cross-linked CS-OrnEt | OrnEt•2HCl | 0.0200 | 0.0800 |
| Compound 40 | (Example 10) | | 0.0300 | 0.120 |
| Compound 41 | | | 0.0325 | 0.130 |
| Compound 42 | | | 0.0350 | 0.140 |
| Compound 43 | Cross-linked CS-Spermidine | Spermidine•3HCl | 0.0100 | 0.0400 |
| Compound 44 | (Example 11) | | 0.0200 | 0.0800 |

1) Compounds 33 to 38 were produced under the following conditions: the equivalent of the cross-linking agent (fixed); the equivalent of DMT-MM (fixed); and reaction time of cross-linking: 2 hours (compound 33), 3 hours (compound 34), 3 hours and 40 minutes (compound 35), 4 hours and 20 minutes (compound 36), 5 hours (compound 37), and 5 hours and 50 minutes (compound 38).

TABLE 3

| Compound | Cross-linked product | Cross-linking agent | Equivalent of cross-linking agent (eq) | Equivalent of DMT-MM (eq) |
|---|---|---|---|---|
| Compound 48 | Cross-linked CS- | triAmine·3HCl | 0.0091 | 0.0364 |
| Compound 49 | triAmine | | 0.0092 | 0.0368 |
| Compound 50 | (Example A1) | | 0.0097 | 0.0388 |
| Compound 51 | Cross-linked CS- | NC3(OH)N·2HCl | 0.0220 | 0.0880 |
| Compound 52 | NC3(OH)N | | 0.0240 | 0.0960 |
| Compound 53 | (Example A2) | | 0.0260 | 0.1040 |
| Compound 54 | Cross-linked CS- | NC4(=)N·2HCl | 0.0270 | 0.1080 |
| Compound 55 | NC4(=)N (Example A3) | | 0.0275 | 0.1100 |
| Compound 56 | Cross-linked CS- | Xylylene·2HCl | 0.0135 | 0.0540 |
| Compound 57 | Xylylene (Example A4) | | 0.0145 | 0.0580 |
| Compound 58 | | | 0.0150 | 0.0600 |
| Compound 59 | Cross-linked CS- | Cyclohex·2HCl | 0.0410 | 0.1640 |
| Compound 60 | Cyclohex (Example A5) | | 0.0425 | 0.1700 |
| Compound 61 | Cross-linked CS- | NC5(S)N·2HCl | 0.0170 | 0.0680 |
| Compound 62 | NC5(S)N (Example A6) | | 0.0180 | 0.0720 |
| Compound 63 | Cross-linked CS- | Glycol(C5)·HCl | 0.0290 | 0.1160 |
| Compound 64 | Glycol(C5) (Example A7) | | 0.0310 | 0.1240 |
| Compound 65 | Cross-linked CS- | Glycol(C11)·2HCl | 0.0380 | 0.1520 |
| Compound 66 | Glycol(C11) (Example A8) | | 0.0410 | 0.1640 |
| Compound 67 | Cross-linked CS- Spermidine (Example 11) | Spermidine·3HCl | 0.0220 | 0.0880 |

TABLE 4

| Compound | Derivative | Cross-linking agent | Equivalent of cross-linking agent (eq) | Equivalent of DCC (eq) |
|---|---|---|---|---|
| Compound 45 | CS-NC12N Derivative | NC12N·2HCl | 0.30 | 0.66 |
| Compound 46 | (Comparative Example) | | 0.60 | 1.32 |
| Compound 47 | (Comparative Example 1) | | 0.90 | 1.98 |

Example 12A

Analysis (Determination of Cross-Linked Structure)

The CS—NC12N derivative produced through the method described in WO 91/16881 was analyzed by various analytic methods. However, the cross-linkage of CS was not determined (C. Bourie, et al., J. Biomater. Appl., 12, (1998), 201-221). For determination of the cross-linkage of the cross-linked CS of the present invention, the cross-linked CS was digested with an enzyme, and the digested product was analyzed by means of liquid chromatography (HPLC)/multi-stage mass spectrometry.

<Test Substance>

CS (CSC, sodium chondroitin sulfate (Japanese Pharmaceutical Codex), weight average molecular weight: 40,000, Seikagaku Corporation) and the cross-linked CS—NC2N (compound 9) were used.

<Method>

(1) Enzymatic Digestion of CS and Cross-Linked CS—NC2N

Chondroitinase ABC (C-ABC) (Seikagaku Corporation) was diluted with 50 mM tris-HCl buffer (pH 7.5)-0.1% BSA solution (50 U/mL). The diluted C-ABC (10 μl) was added to 1% w/v aqueous CS solution (20 μL) or 1% w/v aqueous cross-linked CS—NC2N solution (20 μl). The resultant mixture was heated at 37° C. for three hours and then boiled for 30 seconds, to thereby stop the reaction.

(2) HPLC Analysis of Enzyme-Digested Product

The C-ABC-digested liquid sample was diluted to prepare a solution (200 μL in total), the liquid comprising water and acetonitrile (=1:1 (v/v)). The resultant solution was analyzed by means of an LC-MS apparatus of HPLC (Prominence, manufactured by Shimadzu Corporation) connected to ESI-MS (LCMS-IT-TOF, manufactured by Shimadzu Corporation). TSKgel Amide-80 HR (4.6 mm I.D.×250 mm) was used as a column. 20 mM aqueous ammonium formate solution (Solvent A) and acetonitrile (Solvent B) were used as eluents for analysis of the C-ABC-digested liquid sample (detection: 232 nm and MS). ESI-MS was operated under the following conditions: interface voltage: −3.5 kV, CDL temperature: 200° C., heat block temperature: 200° C., scanning molecular weight range: m/z=300 to 1,500 for MS, m/z=50 to 2,000 for MS".

(3) Multi-Stage Mass Spectrometry of Newly Observed Peak

Peaks observed only in the chart of the cross-linked CS—NC2N through LC-MS analysis were subjected to mass spectrometry under the conditions described below. LCMS-IT-TOF (manufactured by Shimadzu Corporation) connected to a nanoESI ion source (NES-100, manufactured by New Objective) was used for ESI-MS. A solution containing the cross-linked CS—NC2N was fractionated under the aforementioned HPLC conditions, and the solvent was removed from the solution under reduced pressure. Thereafter, the residue was dissolved in a 0.5% $NH_3$-containing 50% MeOH solution. The resultant solution was directly injected by means of a syringe pump. ESI-MS was operated under the following conditions: flow rate: 10 µL/h, interface voltage: −1.5 kV, CDL temperature: 200° C., heat block temperature: 200° C., scanning molecular weight range: m/z=1,300 to 1,500 for MS, m/z=50 to 2,000 for MS".

<Test Results>

The HPLC charts of the digested liquids illustrate that CS and the cross-linked CS—NC2N were similarly digested with C-ABC (FIG. 1). Peaks A and B in FIG. 1 are typical peaks that are not observed in the HPLC chart of non-cross-linked CS. The LC-MS analysis suggested that these peaks belong to a structure having a group in a diamine. Table 5 summarizes structures that are presumed to have a group in a diamine on the basis of mass-to-charge ratio.

Figure 2:
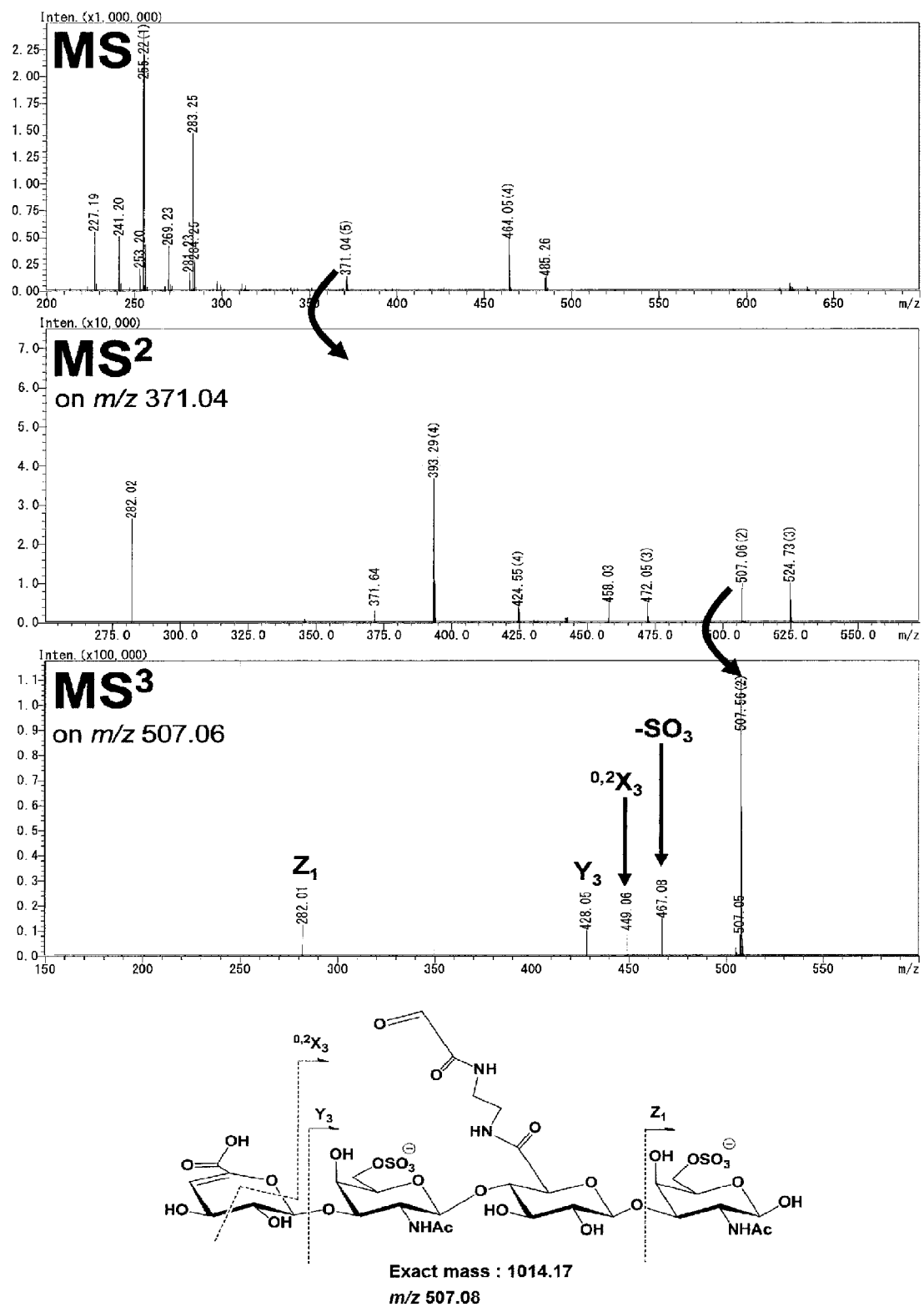
FIG. 2 shows an example of the results of analysis by multi-stage mass spectrometry.
Figure 3:
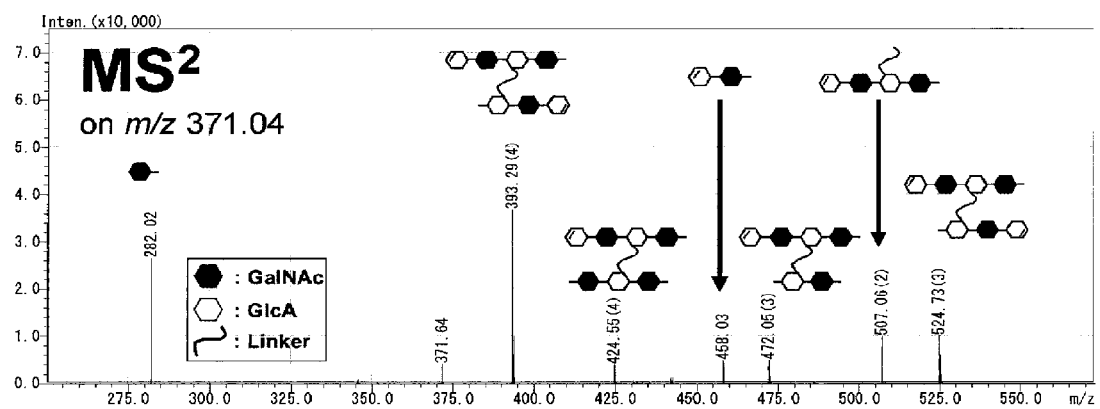
FIG. 3 shows an example of the results of analysis by multi-stage mass spectrometry.

Peak B was subjected to multi-stage mass spectrometry for determining a structure cross-linked with a group in a diamine. FIGS. 2 and 3 illustrate some of the results. As illustrated in FIGS. 2 and 3, peaks suggesting the covalent bonding between ethane-1,2-diamine and two glucuronic acid molecules of CS were detected.

TABLE 5

| | | | Composition | | | | | | |
|---|---|---|---|---|---|---|---|---|---|
| m/z | Valence | M | GalNAc | GlcA | Sulfate group | Crosslinker | Na | Theoretical value | Error (ppm) |
| 710.60 | 2 | 1423.22 | 3 | 3 | 3 | 1 | 1 | 1423.23 | −9.84 |
| 524.75 | 3 | 1577.27 | 3 | 4 | 3 | 1 | 0 | 1577.28 | −3.80 |
| 532.08 | 3 | 1599.26 | 3 | 4 | 3 | 1 | 1 | 1599.26 | 1.25 |
| 592.44 | 3 | 1780.34 | 4 | 4 | 3 | 1 | 0 | 1780.36 | −8.43 |
| 464.07 | 4 | 1860.31 | 4 | 4 | 4 | 1 | 0 | 1860.32 | −1.61 |
| 660.40 | 3 | 1984.22 | 4 | 4 | 5 | 1 | 2 | 1984.24 | −5.54 |
| 806.12 | 3 | 2421.38 | 5 | 5 | 6 | 1 | 1 | 2421.32 | 26.43 |

<Conclusion>

The liquid chromatography/multi-stage mass spectrometry of the enzyme-digested cross-linked CS—NC2N showed the covalent bonding between the diamine and the carboxy groups of two molecules of glucuronic acid. The results demonstrated that the cross-linked CS of the present invention has a cross-linked structure.

Example 12B

Determination of Percent of Cross-Linking

A portion of the sample prepared in Example 1 or 2 was weighed (10 mg) and dissolved in 20 mM sulfuric acid (1 mL) followed by subjected to degassing. The resultant solution was heated at 60° C. for six hours and then basified. Ethanol and propylene oxide were added to the basified solution, and the solution was heated at 60° C. overnight. The solution was cooled and acidified followed by subjected to evaporation to dryness under reduced pressure. Diaminobutane (internal standard) was added to the resultant product, and 6 M hydrochloric acid was added thereto. The resultant solution was heated at 110° C. overnight followed by subjected to evaporation to dryness under reduced pressure. A mixture of dimethyl sulfoxide and water (=3:1) was added to the resultant product, and the mixture was shaken for 30 minutes. The resultant mixture was transferred to another container, and triethylamine and a mixture of phenyl isothiocyanate and acetonitrile (=1:9) were added to the mixture. The mixture was vigorously agitated and then heated at 30° C. for 20 minutes. The mixture was passed through a 0.22-µm filter, and then subjected to analysis by means of LC-ESI-MS (positive mode). Gemini-NX 3 µm C18 2×50 mm was used as a column. $H_2O$ (Solvent A), MeCN (Solvent B), and 100 mM $NH_4HCO_3$ (pH 10.0 by $NH_4OH$) (Solvent C) were used as eluents for analysis. The results are illustrated in Table 6.

TABLE 6

| Compound | Cross-linked product | Equivalent of cross-linking agent (eq) | Percent of cross-linking (%) |
|---|---|---|---|
| Compound 2 | Cross-linked CS-NC2N | 0.0050 | 0.064 |
| Compound 10 | | 0.02375 | 0.59 |
| Compound 8 | | 0.0275 | 0.89 |

Example 13

Preparation of Composition Containing Cross-Linked CS

Phosphate buffered saline (may be referred to as "PBS" herein) having the following composition was prepared:
0.065% (w/v) sodium dihydrogen phosphate dihydrate
0.03% (w/v) disodium hydrogen phosphate dodecahydrate
0.9% (w/v) sodium chloride.

The cross-linked CS products produced in Examples 1, 2, 4, 6 to 11, and A1 to A8 were mixed with the aforementioned PBS so as to achieve concentrations as shown in Tables 7, 8, and 9, followed by shaking with a shaking apparatus overnight, to thereby prepare samples (samples 1 to 43, 55 to 71, and 75 to 77). Thereafter, some samples were measured for absorbance at 600 nm by means of an ultraviolet visible spectrophotometer (UV-1800, manufactured by Shimadzu Corporation). The results are illustrated in Tables 7, 8, and 9.

Comparative Example 2

Preparation of Composition Containing CS

In the same manner as described in Example 13, CS (CSC [Seikagaku Corporation] and CSA [Sigma-Aldrich]) was mixed with the PBS so as to achieve concentrations as shown in Table 10, to thereby prepare samples (samples 47 to 54). Thereafter, sample 53 was measured for absorbance at 600 nm by means of an ultraviolet visible spectrophotometer (UV-1800, manufactured by Shimadzu Corporation). The results are illustrated in Table 10.

Comparative Example 3

Preparation of Composition Containing CS—NC12N Derivative (Comparative Example)

In the same manner as described in Example 13, the CS—NC12N derivative (Comparative Example) produced in Comparative Example 1 was mixed with the PBS so as to achieve concentrations as shown in Table 8, to thereby prepare samples (samples 44 to 46 and 72 to 74). Thereafter, the samples were measured for absorbance at 600 nm by means of an ultraviolet visible spectrophotometer (UV-1800, manufactured by Shimadzu Corporation). The results are illustrated in Table 8.

Example 14

Measurement of Viscosities of Samples

The viscosities (mPa·s) of the samples prepared in Example 13 and Comparative Example 2 were measured at 25° C. and 5 rpm by means of an E-type rotary viscometer (TV-L/H, Toki Sangyo Co., Ltd.) with a standard cone (CORD-1, 1° 34'×R24). If the viscosity at 5 rpm fell outside the range of detection, an extrapolated value was determined at another rotation speed, and the value was defined as viscosity (mPa·s). The results are illustrated in Tables 7 to 10.

TABLE 7

| Sample | Compound | Concentration of cross-linked CS (wt %) | Viscosity (mPa · s) | Absorbance (Abs) | Solution form (clear/turbid) |
|---|---|---|---|---|---|
| Sample 1 | Compound 2 | 2.00 | 7 | — | — |
| Sample 2 | | 3.82 | 18 | — | — |
| Sample 3 | | 6.00 | 58 | — | — |
| Sample 4 | | 8.00 | 132 | — | — |
| Sample 5 | | 10.00 | 274 | — | — |
| Sample 6 | | 12.00 | 493 | — | — |
| Sample 7 | | 14.00 | 936 | 0.011 | clear |
| Sample 8 | Compound 3 | 2.00 | 8 | — | — |
| Sample 9 | | 4.00 | 29 | — | — |
| Sample 10 | | 6.00 | 83 | — | — |
| Sample 11 | | 8.00 | 199 | — | — |
| Sample 12 | | 10.00 | 441 | — | — |
| Sample 13 | | 12.00 | 890 | 0.007 | clear |
| Sample 14 | Compound 4 | 2.00 | 12 | — | — |
| Sample 15 | | 5.00 | 94 | — | — |
| Sample 16 | | 10.00 | 1245 | 0.014 | clear |
| Sample 17 | Compound 5 | 2.00 | 15 | — | — |
| Sample 18 | | 5.00 | 161 | — | — |
| Sample 19 | | 10.03 | 2360 | 0.013 | clear |
| Sample 20 | Compound 1 | 1.97 | 32 | — | — |
| Sample 21 | | 5.00 | 367 | — | — |
| Sample 22 | | 10.00 | 3000 | 0.010 | clear |
| Sample 23 | Compound 6 | 1.00 | 33 | — | — |
| Sample 24 | | 2.03 | 115 | — | — |
| Sample 25 | | 5.00 | 1306 | — | — |
| Sample 26 | | 7.49 | 4340 | 0.025 | clear |
| Sample 27 | | 0.50 | 25 | — | — |
| Sample 28 | Compound 7 | 1.00 | 156 | — | — |

TABLE 7-continued

| Sample | Compound | Concentration of cross-linked CS (wt %) | Viscosity (mPa·s) | Absorbance (Abs) | Solution form (clear/turbid) |
|---|---|---|---|---|---|
| Sample 29 | | 2.00 | 673 | — | — |
| Sample 30 | | 4.00 | 2880 | — | — |
| Sample 31 | | 6.00 | 8190 | 0.020 | clear |
| Sample 32 | Compound 8 | 0.50 | 139 | — | — |
| Sample 33 | | 1.00 | 646 | — | — |
| Sample 34 | | 2.00 | 2800 | — | — |
| Sample 35 | | 4.00 | 10649 | 0.020 | clear |
| Sample 36 | Compound 10 | 2.00 | 52 | 0.009 | clear |

—: No data

TABLE 8

| Sample | Compound | Concentration of cross-linked CS/derivative (wt %) | Viscosity (mPa·s) | Absorbance (Abs) | Solution form (clear/turbid) |
|---|---|---|---|---|---|
| Sample 37 | Compound 18 | 8.00 | 3770 | 0.025 | clear |
| Sample 38 | Compound 26 | 8.75 | 4000 | 0.033 | clear |
| Sample 39 | Compound 30 | 8.00 | 3330 | 0.018 | clear |
| Sample 40 | Compound 32 | 5.00 | 3740 | 0.014 | clear |
| Sample 41 | Compound 36 | 7.50 | 3600 | — | — |
| Sample 42 | Compound 42 | 8.25 | 3200 | 0.028 | clear |
| Sample 43 | Compound 44 | 7.50 | 3230 | — | — |
| Sample 44 | Compound 45 | 2.00 | — | 2.923 | turbid |
| Sample 45 | Compound 46 | 2.00 | — | 2.034 | turbid |
| Sample 46 | Compound 47 | 2.00 | — | 1.457 | turbid |
| Sample 72 | Compound 45 | 0.40 | — | 1.352 | turbid |
| Sample 73 | Compound 46 | 0.40 | — | 0.417 | turbid |
| Sample 74 | Compound 47 | 0.40 | — | 0.238 | turbid |

—: No data

TABLE 9

| Sample | Compound | Concentration of cross-linked CS (wt %) | Viscosity (mPa·s) | Absorbance (Abs) | Solution form (clear/turbid) |
|---|---|---|---|---|---|
| Sample 55 | Compound 48 | 2.00 | 38 | 0.003 | clear |
| Sample 56 | Compound 49 | 2.00 | 60 | 0.008 | clear |
| Sample 57 | Compound 50 | 2.00 | 122 | 0.001 | clear |
| Sample 58 | Compound 51 | 2.00 | 27 | 0.005 | clear |
| Sample 59 | Compound 52 | 2.00 | 62 | 0.000 | clear |
| Sample 60 | Compound 53 | 2.00 | 130 | 0.002 | clear |
| Sample 61 | Compound 54 | 2.00 | 42 | 0.004 | clear |
| Sample 62 | Compound 55 | 2.00 | 98 | 0.003 | clear |
| Sample 63 | Compound 56 | 2.00 | 45 | 0.001 | clear |
| Sample 64 | Compound 57 | 2.00 | 72 | 0.003 | clear |
| Sample 65 | Compound 58 | 2.00 | 191 | 0.004 | clear |
| Sample 66 | Compound 59 | 2.00 | 49 | 0.002 | clear |
| Sample 67 | Compound 60 | 2.00 | 88 | 0.001 | clear |
| Sample 68 | Compound 61 | 2.00 | 44 | 0.000 | clear |
| Sample 69 | Compound 62 | 2.00 | 100 | 0.001 | clear |
| Sample 70 | Compound 63 | 2.00 | 50 | 0.002 | clear |
| Sample 71 | Compound 64 | 2.00 | 123 | 0.005 | clear |
| Sample 75 | Compound 65 | 2.00 | 51 | 0.002 | clear |
| Sample 76 | Compound 66 | 2.00 | 157 | 0.010 | clear |
| Sample 77 | Compound 67 | 2.00 | 85 | 0.003 | clear |

TABLE 10

| Sample | Compound | Concentration of CS (wt %) | Viscosity (mPa·s) | Absorbance (Abs) | Solution form (clear/turbid) |
|---|---|---|---|---|---|
| Sample 47 | CS | 2.00 | 5 | — | — |
| Sample 48 | | 4.00 | 18 | — | — |
| Sample 49 | | 6.00 | 47 | — | — |
| Sample 50 | | 8.00 | 100 | — | — |
| Sample 51 | | 10.00 | 200 | — | — |
| Sample 52 | | 12.49 | 423 | — | — |
| Sample 53 | | 14.99 | 822 | 0.002 | clear |
| Sample 54 | CSA | 2.00 | — | — | — |

—: No data

<Conclusion>

Samples 7, 13, 16, 19, 22, 26, 31, 35 to 40, 42, 53, 55 to 71, and 75 to 77 were found to be in a clear solution form (i.e., these samples were an aqueous solution). When a composition of higher concentration is in a clear solution form, a composition of lower concentration is also probably in a clear solution form. Samples 1 to 43, 47 to 71, and 75 to 77 were confirmed to be clear through visual observation (the term "clear" as used herein refers to a clear composition). In contrast, compositions containing the CS—NC12N derivative (Comparative Example) (compounds 45 to 47) were found to be in a turbid solution form (i.e., these compositions were not an aqueous solution).

Example 15

Test for Filter-Passing Rate

Some of the samples prepared in Example 13 were subjected to the test for filter-passing rate. Specifically, a sample was charged into a 1 mL syringe (SS-01T, Terumo Corporation) equipped with a porous filter (pore size: 5.0 μm, diameter: 25 mm, Millex (registered trademark)-SV 5.00 μm (Millipore Ireland)). The sample was extruded with a piston at 25° C. and a pressure of 5.3 kgf/cm² or less, to thereby pass the sample through the filter. The CS concentration of the sample was determined before passage of the sample through the filter. Also, the CS concentration of the sample was determined after passage of the sample (in an amount of 0.5 mL or more) through the filter. The CS concentration was determined by the carbazole-sulfuric acid method using 20.0 μg/mL aqueous D-glucuronolactone solution as a standard. The ratio of the CS concentration after passage of the sample through the filter to that before passage of the sample through the filter was calculated, to thereby determine the filter-passing rate of the sample. The results are illustrated in Table 11.

TABLE 11

| Sample | Compound | Concentration of cross-linked CS (wt %) | Viscosity (mPa·s) | Passing rate (%) |
|---|---|---|---|---|
| Sample 36 | Compound 10 | 2.00 | 52 | 99 |
| Sample 22 | Compound 1 | 10.00 | 3000 | 96 |
| Sample 26 | Compound 6 | 7.49 | 4340 | 97 |
| Sample 31 | Compound 7 | 6.00 | 8190 | 99 |
| Sample 35 | Compound 8 | 4.00 | 10649 | 95 |
| Sample 30 | Compound 7 | 4.00 | 2880 | >99 |
| Sample 34 | Compound 8 | 2.00 | 2800 | 89 |
| Sample 55 | Compound 48 | 2.00 | 38 | >99 |
| Sample 56 | Compound 49 | 2.00 | 60 | >99 |
| Sample 57 | Compound 50 | 2.00 | 122 | 98 |
| Sample 58 | Compound 51 | 2.00 | 27 | >99 |
| Sample 59 | Compound 52 | 2.00 | 62 | 98 |
| Sample 60 | Compound 53 | 2.00 | 130 | 97 |
| Sample 61 | Compound 54 | 2.00 | 42 | 99 |
| Sample 62 | Compound 55 | 2.00 | 98 | 98 |
| Sample 63 | Compound 56 | 2.00 | 45 | >99 |
| Sample 64 | Compound 57 | 2.00 | 72 | >99 |
| Sample 65 | Compound 58 | 2.00 | 191 | 96 |
| Sample 66 | Compound 59 | 2.00 | 49 | >99 |
| Sample 67 | Compound 60 | 2.00 | 88 | >99 |
| Sample 68 | Compound 61 | 2.00 | 44 | 95 |
| Sample 69 | Compound 62 | 2.00 | 100 | >99 |
| Sample 70 | Compound 63 | 2.00 | 50 | 96 |
| Sample 71 | Compound 64 | 2.00 | 123 | >99 |
| Sample 75 | Compound 65 | 2.00 | 51 | >99 |
| Sample 76 | Compound 66 | 2.00 | 157 | 99 |
| Sample 77 | Compound 67 | 2.00 | 85 | >99 |

<Conclusion>

The results demonstrated that the samples prepared in Example 13 exhibit a filter-passing rate of 80% or more.

Example 16

Examination for Effect of Cross-Linked CS in Accelerating Healing of Corneal Epithelial Disorder (1)

SD rats (Charles River Laboratories Japan, Inc.) were prepared into dry eye models in accordance with the method described in Fujihara, et al. (Invest. Ophthalmol. Vis. Sci. 42 (1): 96-100 (2001)). A test substance was instilled into the eyes of each model and examined for the effect of accelerating the healing of corneal epithelial disorder.

<Test Substance>

CS (CSC, sodium chondroitin sulfate (Japanese Pharmaceutical Codex), weight average molecular weight: 40,000, Seikagaku Corporation), compound 10, compound 18, or compound 42 was mixed with PBS so as to achieve a CS (or cross-linked CS) concentration of 2%, and the mixture was shaken by means of a shaking apparatus overnight, to thereby prepare a test substance. The test substance was 2% CS, 2% cross-linked CS—NC2N, 2% cross-linked CS—NC4N, or 2% cross-linked CS-OrnEt. PBS was used as a control.

<Method>

(1) Preparation of Dry Eye Model

The exorbital lacrimal gland was excised from both eyes of an SD rat under inhalation anesthesia with isoflurane, to thereby prepare a dry eye model.

(2) Ocular Instillation of Test Substance

About eight weeks after the preparation of the model, a portion of corneal epithelial disorder was stained with fluorescein. The degree of staining at an upper, middle, or lower portion of the superficial cornea was scored according to the following classification, and the total scores of each portion were calculated. For an individual exhibiting a binocular average score of 5 or more, the test substance was instilled into both eyes (5 μL per an eye) twice a day for three weeks. PBS serving as a control was instilled in the same manner as described above.

<Criteria for Determination>
  Score 0: No dot stained
  Score 1: Sparse (fluorescein staining dots are distant from each other)
  Score 2: Moderate (intermediate between scores 1 and 3)
  Score 3: Dense (most of fluorescein staining dots are close each other)

(3) Evaluation for Effect of Healing Corneal Epithelial Disorder

One, two, and three weeks after the initiation of ocular instillation, the effect of healing corneal epithelial disorder was scored according to the method described in (2) above.

(4) Statistical Analysis

One, two, and three weeks after the initiation of ocular instillation, the difference in averaged score between PBS and the test substance was analyzed by t-test with a significance level of 5% (two-sided).

<Test Results>

Figure 4:
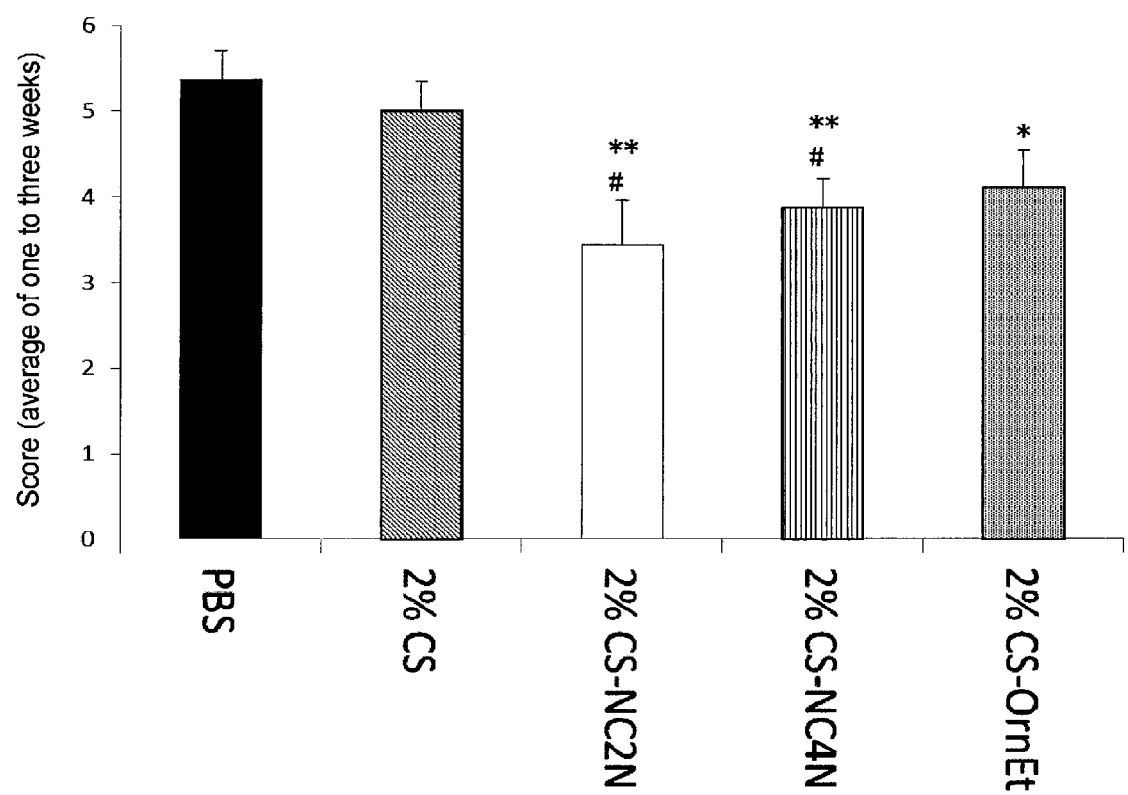
FIG. 4 shows a graph illustrating an average degree of fluorescein staining in the case of ocular instillation into an animal model twice a day.

Table 12 and FIG. 4 illustrate the transitions and averages of scores for one, two, and three weeks. 2% Cross-linked CS—NC2N, 2% cross-linked CS—NC4N, and 2% cross-linked CS-OrnEt exhibited a significant effect of accelerating the healing of corneal epithelial disorder as compared with PBS. 2% Cross-linked CS—NC2N and 2% cross-linked CS—NC4N exhibited a significant effect of accelerating the healing of corneal epithelial disorder as compared with 2% CS.

<Test Results>

Figure 5:
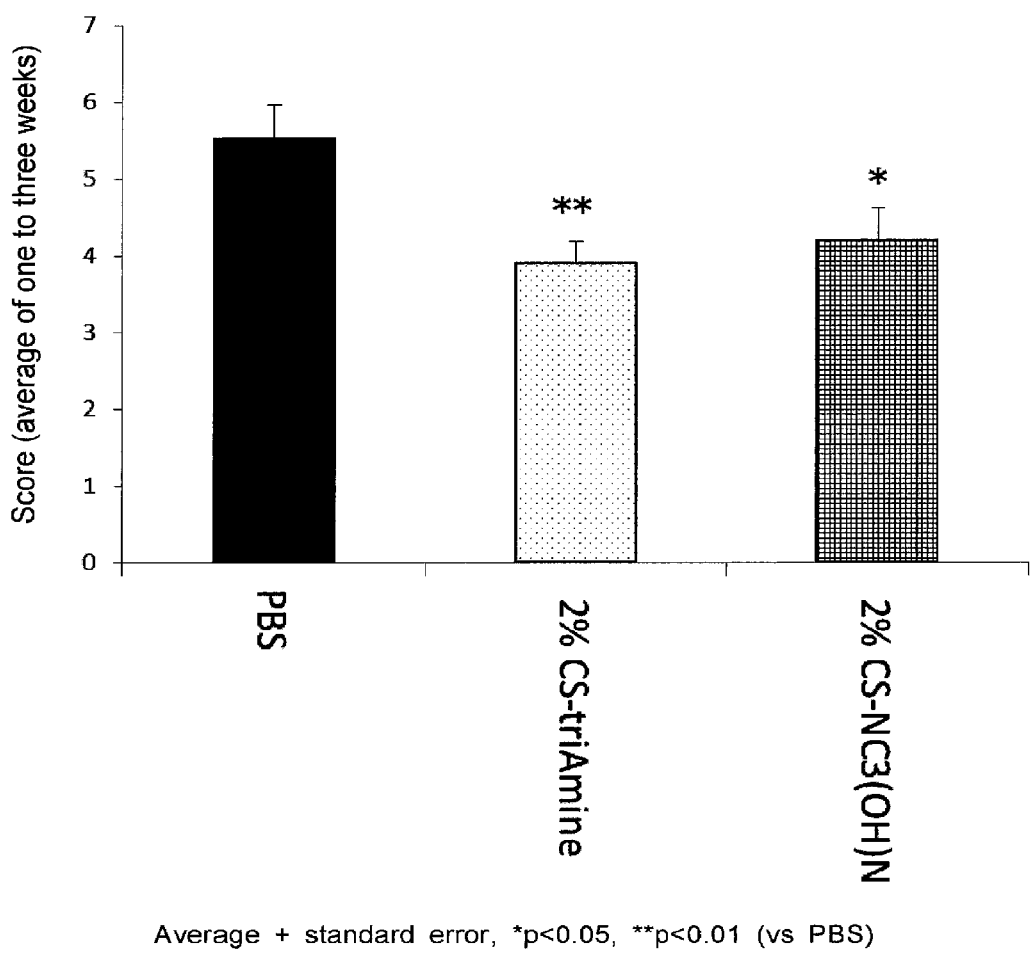
FIG. 5 shows a graph illustrating an average degree of fluorescein staining in the case of ocular instillation into an animal model twice a day.
Figure 6:
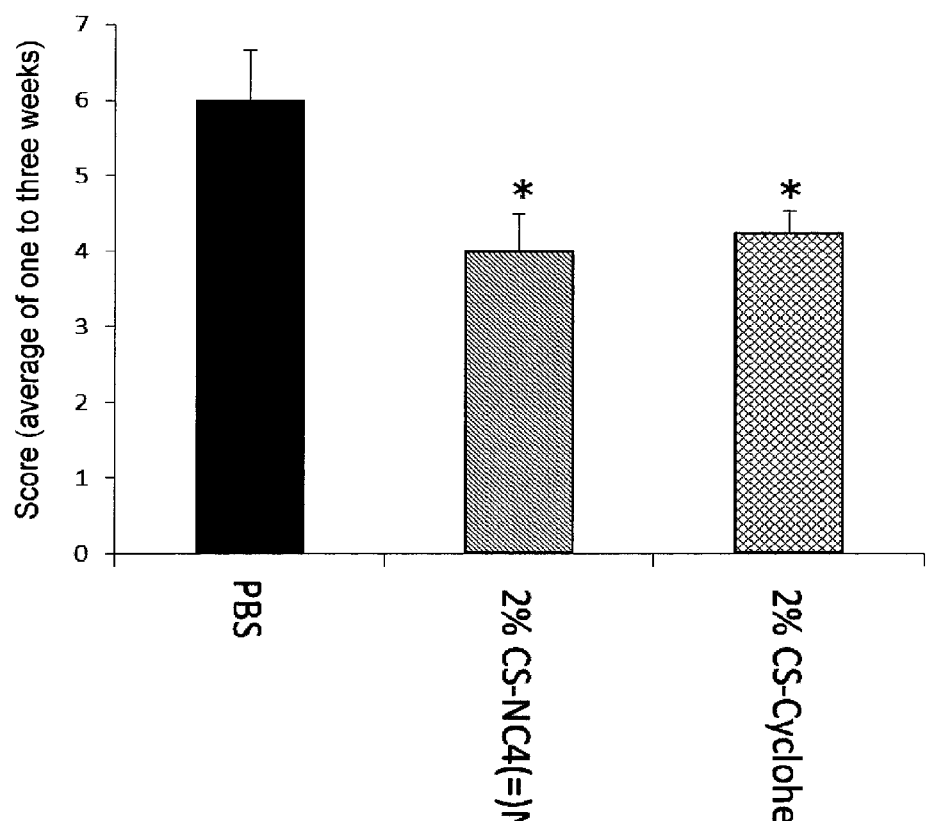
FIG. 6 shows a graph illustrating an average degree of fluorescein staining in the case of ocular instillation into an animal model twice a day.

Table 13 and FIG. 5 (Example 17A) and Table 14 and FIG. 6 (Example 17B) illustrate the transitions and averages of scores for one, two, and three weeks. 2% Cross-linked CS-triAmine, 2% cross-linked CS—NC3(OH)N, 2% cross-linked CS—NC4(=)N, and 2% cross-linked CS-Cyclohex exhibited a significant effect of accelerating the healing of corneal epithelial disorder as compared with PBS.

TABLE 13

|  | PBS | 2% CS-triAmine | 2% CS-NC3(OH)N |
| --- | --- | --- | --- |
| Before ocular instillation | 7.0 ± 0.8 | 6.9 ± 0.6 | 7.4 ± 0.8 |
| 1 week after | 6.0 ± 0.8 | 4.0 ± 0.6 | 6.3 ± 0.6 |
| 2 weeks after | 5.4 ± 0.3 | 4.1 ± 0.8 | 3.8 ± 0.8 |
| 3 weeks after | 5.2 ± 0.5 | 3.6 ± 0.8 | 2.5 ± 0.3 |
| n number | n = 10 | n = 10 | n = 10 |

Average ± standard error

TABLE 14

|  | PBS | 2% CS-NC4(=)N | 2% CS-Cyclohex |
| --- | --- | --- | --- |
| Before ocular instillation | 6.7 ± 0.5 | 6.7 ± 0.4 | 6.7 ± 0.5 |
| 1 week after | 5.9 ± 0.6 | 4.0 ± 0.4 | 4.1 ± 0.3 |
| 2 weeks after | 5.7 ± 0.8 | 4.6 ± 0.8 | 4.1 ± 0.4 |
| 3 weeks after | 6.4 ± 0.8 | 3.4 ± 0.7 | 4.5 ± 0.6 |
| n number | n = 10 | n = 10 | n = 10 |

Average ± standard error

TABLE 12

|  | PBS | 2% CS | 2% CS-NC2N | 2% CS-NC4N | 2% CS-OrnEt |
| --- | --- | --- | --- | --- | --- |
| Before ocular instillation | 6.8 ± 0.5 | 6.2 ± 0.4 | 6.6 ± 0.5 | 6.4 ± 0.4 | 6.6 ± 0.4 |
| 1 week after | 5.0 ± 0.7 | 5.1 ± 0.5 | 4.0 ± 0.9 | 4.8 ± 0.4 | 5.1 ± 0.7 |
| 2 weeks after | 5.6 ± 0.5 | 4.7 ± 0.5 | 3.1 ± 0.7 | 3.2 ± 0.4 | 4.0 ± 0.6 |
| 3 weeks after | 5.5 ± 0.5 | 5.2 ± 0.4 | 3.2 ± 0.5 | 3.6 ± 0.6 | 3.2 ± 0.4 |
| n number | n = 10 | n = 10 | n = 10 | n = 10 | n = 10 |

Average ± standard error

Example 17

Examination for Effect of Cross-Linked CS in Accelerating Healing of Corneal Epithelial Disorder (2)

The effect of accelerating the healing of corneal epithelial disorder was examined in the same manner as described in Example 16.

<Test Substance>

Compound 49 or compound 52 was mixed with PBS so as to achieve a cross-linked CS concentration of 2%, and the mixture was shaken by means of a shaking apparatus overnight, to thereby prepare a test substance. The test substance was 2% cross-linked CS-triAmine and 2% cross-linked CS—NC3(OH)N. PBS was used as a control (Example 17A).

Compound 55 or compound 60 was mixed with PBS in the same manner as described above, to thereby prepare a test substance. The test substance was 2% cross-linked CS—NC4(=)N and 2% cross-linked CS-Cyclohex. PBS was used as a control (Example 17B).

Example 18

Examination for Effect of Cross-Linked CS in Accelerating Healing of Corneal Epithelial Disorder (3)

The effect of accelerating the healing of corneal epithelial disorder was examined in the same manner as described in Example 16.

<Test Substance>

Compound 26, compound 62, compound 64, compound 66, or compound 67 was mixed with PBS so as to achieve a cross-linked CS concentration of 2%, and the mixture was shaken by means of a shaking apparatus overnight, to thereby prepare a test substance. The test substance was 2% cross-linked CS—NC6N, 2% cross-linked CS—NC5(S)N, 2% cross-linked CS-Glycol(C5), 2% cross-linked CS-Glycol(C11), and 2% cross-linked CS-Spermidine. PBS was used as a control (Examples 18A to 18D).

<Test Results>

Figure 7:
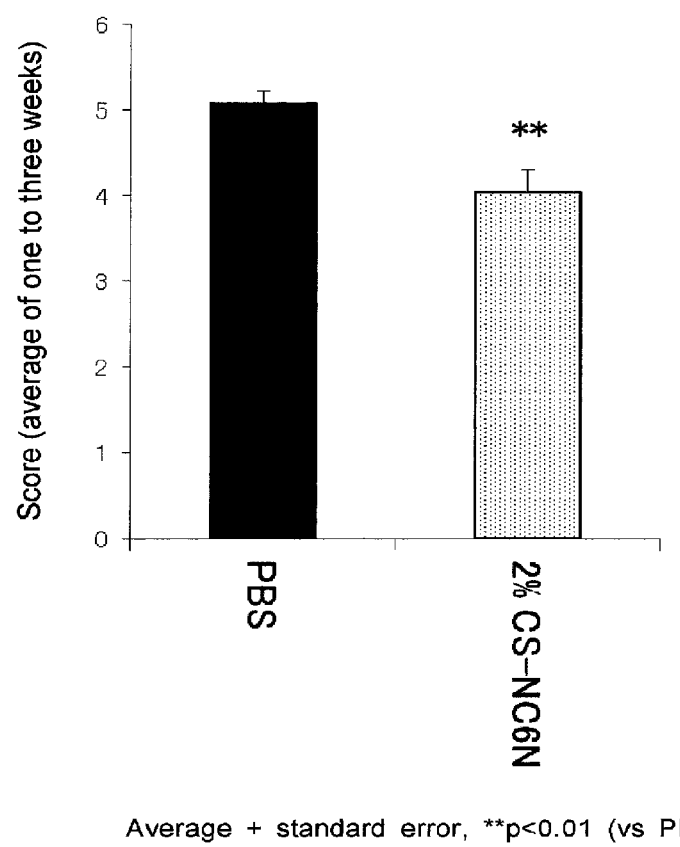
FIG. 7 shows a graph illustrating an average degree of fluorescein staining in the case of ocular instillation into an animal model twice a day.
Figure 8:
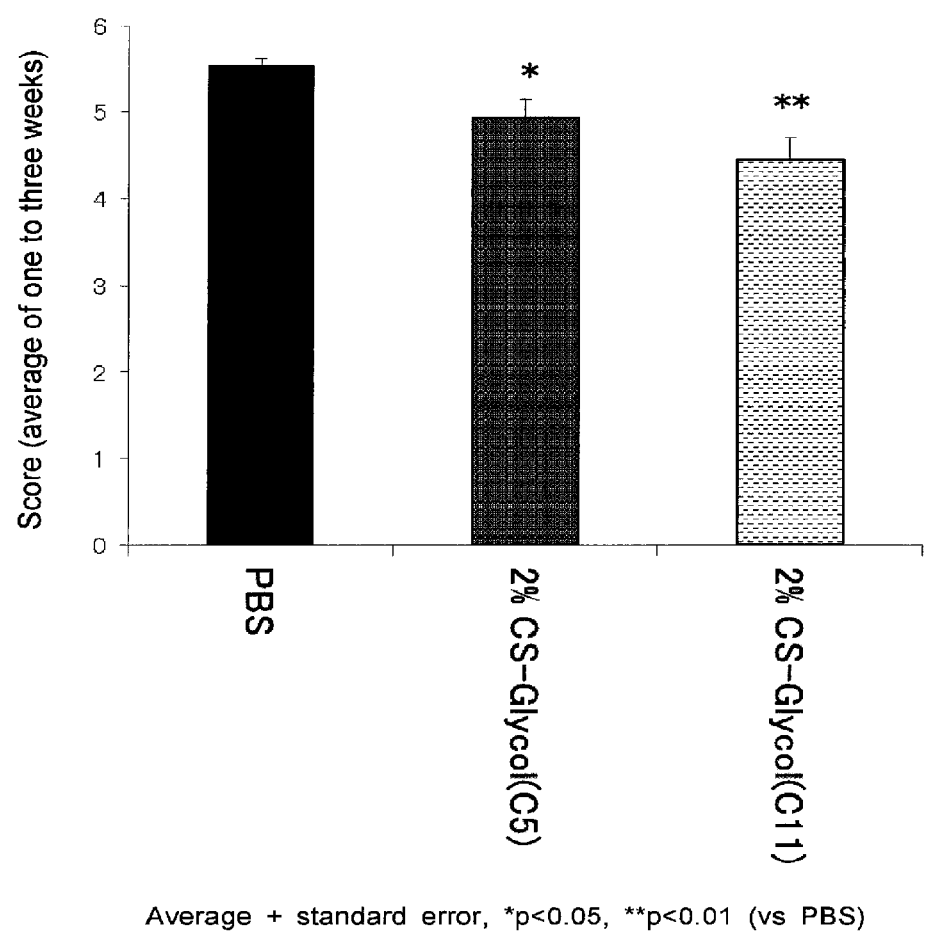
FIG. 8 shows a graph illustrating an average degree of fluorescein staining in the case of ocular instillation into an animal model twice a day.
Figure 9:
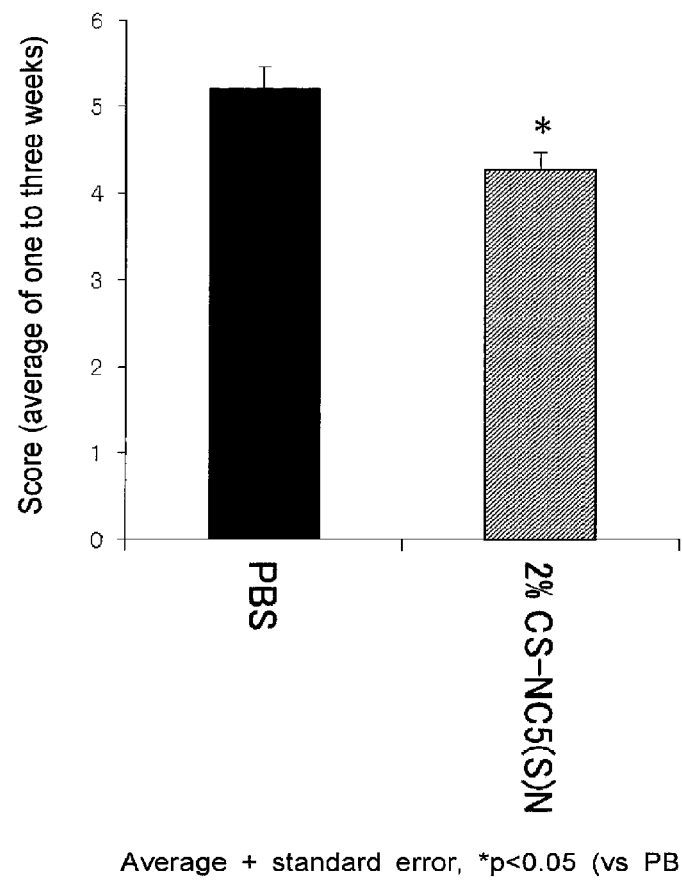
FIG. 9 shows a graph illustrating an average degree of fluorescein staining in the case of ocular instillation into an animal model twice a day.
Figure 10:
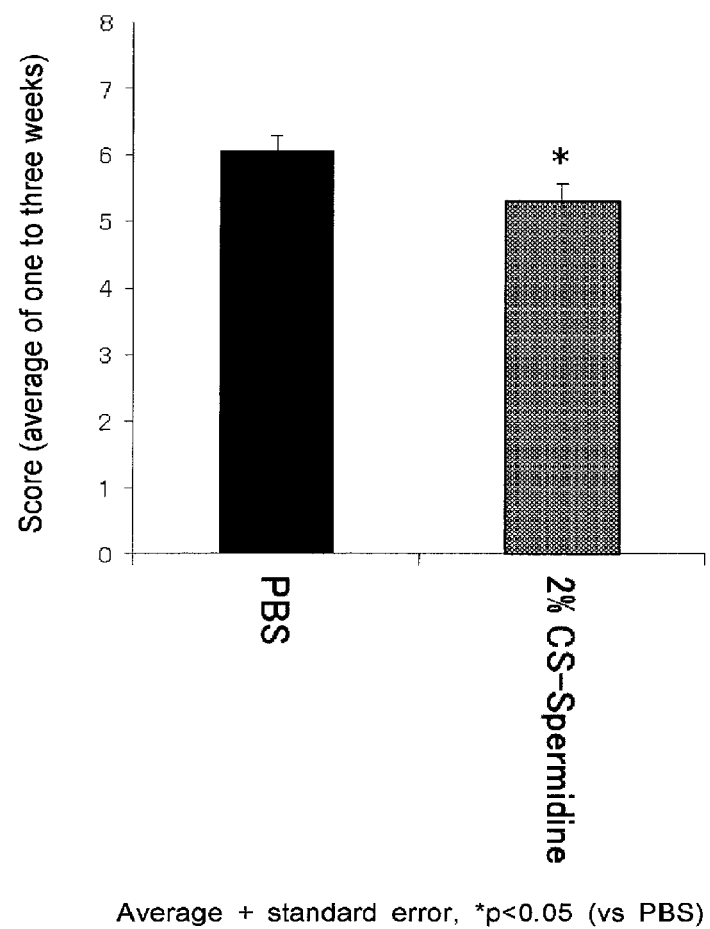
FIG. 10 shows a graph illustrating an average degree of fluorescein staining in the case of ocular instillation into an animal model twice a day.

Table 15 and FIG. 7 (Example 18A), Table 16 and FIG. 8 (Example 18B), Table 17 and FIG. 9 (Example 18C), and Table 18 and FIG. 10 (Example 18D) illustrate the transitions and averages of scores for one, two, and three weeks. 2% Cross-linked CS—NC6N, 2% cross-linked CS—NC5(S)N, 2% cross-linked CS-Glycol(C5), 2% cross-linked CS-Glycol(C11), and 2% cross-linked CS-Spermidine exhibited a significant effect of accelerating the healing of corneal epithelial disorder as compared with PBS. The averages of scores for one, two, and three weeks of 2% cross-linked CS-Glycol(C11) were lower than those of 2% cross-linked CS-Glycol(C5). The results demonstrated that a larger number of oxygen atoms in the main chain leads to a stronger effect of accelerating the healing of corneal epithelial disorder.

TABLE 15

|  | PBS | 2% CS-NC6N |
| --- | --- | --- |
| Before ocular instillation | 5.7 ± 0.3 | 5.8 ± 0.3 |
| 1 week after | 4.9 ± 0.4 | 3.8 ± 0.5 |
| 2 weeks after | 5.2 ± 0.3 | 3.9 ± 0.4 |
| 3 weeks after | 5.1 ± 0.3 | 4.4 ± 0.3 |
| n number | n = 10 | n = 10 |

Average ± standard error

TABLE 16

|  | PBS | 2% CS-Glycol(C5) | 2% CS-Glycol(C11) |
| --- | --- | --- | --- |
| Before ocular instillation | 5.8 ± 0.2 | 5.7 ± 0.2 | 5.3 ± 0.3 |
| 1 week after | 5.6 ± 0.2 | 5.0 ± 0.3 | 4.7 ± 0.4 |
| 2 weeks after | 5.4 ± 0.2 | 4.8 ± 0.3 | 4.3 ± 0.4 |
| 3 weeks after | 5.6 ± 0.2 | 5.0 ± 0.2 | 4.3 ± 0.2 |
| n number | n = 10 | n = 10 | n = 6 |

Average ± standard error

TABLE 17

|  | PBS | 2% CS-NC5(S)N |
| --- | --- | --- |
| Before ocular instillation | 6.1 ± 0.3 | 6.1 ± 0.3 |
| 1 week after | 5.5 ± 0.3 | 4.7 ± 0.3 |
| 2 weeks after | 4.8 ± 0.2 | 4.0 ± 0.3 |
| 3 weeks after | 5.3 ± 0.4 | 4.1 ± 0.2 |
| n number | n = 10 | n = 10 |

Average ± standard error

TABLE 18

|  | PBS | 2% CS-Spermidine |
| --- | --- | --- |
| Before ocular instillation | 6.7 ± 0.2 | 6.8 ± 0.3 |
| 1 week after | 5.8 ± 0.2 | 5.5 ± 0.3 |
| 2 weeks after | 6.4 ± 0.3 | 5.3 ± 0.3 |
| 3 weeks after | 6.0 ± 0.4 | 5.1 ± 0.4 |
| n number | n = 10 | n = 10 |

Average ± standard error

<Conclusion>

As illustrated above, the cross-linked CS of the present invention can be used as an agent for the treatment of an eye disease, in particular, an agent for the therapy of a corneal epithelial disorder and/or dry eye.

INDUSTRIAL APPLICABILITY

The cross-linked CS of the present invention or a composition containing the same can be industrially used as an agent for the treatment of an eye disease. In addition, the method of the present invention can be industrially used as a method for the treatment of an eye disease.

I claim:

1. A method for producing a cross-linked chondroitin sulfate or a pharmaceutically acceptable salt thereof, the method comprising:
    reacting a chondroitin sulfate or pharmaceutically acceptable salt thereof with an amine having two or more primary amino groups in a solvent comprising a condensing agent to obtain the crosslinked chondroitin sulfate or a pharmaceutically acceptable salt thereof,
    wherein a mole equivalent of the amine is from 0.005 to 0.250 relative to 1.00 mole equivalent of disaccharide unit of the chondroitin sulfate or pharmaceutically acceptable salt thereof, and
    wherein the amine has a biodegradable moiety represented by the following formula (II) in a main chain thereof:

—C(=O)-D-  (II)

wherein, in the formula (II), D represents an oxygen atom or a sulfur atom.

2. The method according to claim 1, wherein a percent of cross-linking of the cross-linked chondroitin sulfate or the pharmaceutically acceptable salt thereof is from 0.01% to 30%.

3. The method according to claim 2, wherein the percent of cross-linking of the cross-linked chondroitin sulfate or the pharmaceutically acceptable salt thereof is from 0.05% to 10%.

4. The method according to claim 3, wherein the percent of cross-linking of the cross-linked chondroitin sulfate or the pharmaceutically acceptable salt thereof is from 0.1% to 5%.

5. The method according to claim 1, wherein the condensing agent is 4-(4, 6-dimethoxy-1, 3, 5-triazin-2-yl)-4-methylmorpholinium chloride.

6. The method according to claim 1, wherein a mole equivalent of the condensing agent is from A, wherein A=0.05×valence of the amine, to B, wherein B=5.00× valence of the amine, relative to 1.00 mole equivalent of the amine.

7. The method according to claim 1, wherein the solvent is water or a mixture of water and a water-miscible organic solvent.

8. The method according to claim 7, wherein the water-miscible organic solvent is at least one selected from the group consisting of methanol, ethanol, isopropanol, n-propanol, tertiary butanol, ethylene glycol monomethyl ether, ethyleneglycol monoethyl ether, acetone, 1,4-dioxane, tetrahydrofuran and acetonitrile.

9. The method according to claim 1, wherein the amine is a diamine.

UNITED STATES PATENT AND TRADEMARK OFFICE
CERTIFICATE OF CORRECTION

PATENT NO. : 10,716,804 B2
APPLICATION NO. : 16/536779
DATED : July 21, 2020
INVENTOR(S) : Funayama It is certified that error appears in the above-identified patent and that said Letters Patent is hereby corrected as shown below:

On the Title Page

Item (56) References Cited, OTHER PUBLICATIONS (Column 2, Line 9), "Ey" should read --Eye--.

Item (56) References Cited, OTHER PUBLICATIONS (Column 2, Line 15), "Phramacotherapies" should read --Pharmacotherapies--.

Item (56) References Cited, OTHER PUBLICATIONS (Column 2, Line 29), "International Search Report issued in WIPO Patent Application No." should read --International Search Report issued in WIPO Patent Application No. PCT/JP2016/051176, dated Mar. 29, 2016.--.

Item (56) References Cited, OTHER PUBLICATIONS (Column 2, Line 33), "Caratract" should read --Cataract--.

Item (56) References Cited, OTHER PUBLICATIONS (Column 2, Line 39), "* cited by examiner PCT/JP2016/051176, dated Mar. 29, 2016." should read --* cited by examiner--.

In the Specification

Column 9, Line 32, "amine" should read --amine.--.

Column 13, Line 10, "—(CH2)$_3$—," should read -- —(CH2)$_8$—,--.

Column 13, Lines 14-15, "-CH$_2$CH$_2$O-CH$_2$CH$_2$-CH$_2$CH$_2$-CH$_2$CH$_2$-," should read -- -CH$_2$CH$_2$-O-CH$_2$CH$_2$-O-CH$_2$CH$_2$-O-CH$_2$CH$_2$-,--.

Column 32, Table 7, "Sample 27" should read --Sample 27 Compound 7--.

Column 32, Table 7, "Sample 28 Compound 7" should read --Sample 28--.

Signed and Sealed this
Thirteenth Day of October, 2020

Andrei Iancu
*Director of the United States Patent and Trademark Office*

CERTIFICATE OF CORRECTION (continued)
U.S. Pat. No. 10,716,804 B2

In the Claims

Column 40, Lines 42-43, Claim 5, "4-(4, 6-dimethoxy-1, 3, 5-triazin-2-yl-4-methylmorpholinium" should read --4-(4,6-dimethoxy-1,3,5-triazin-2-yl-4-methylmorpholinium--.

Column 40, Line 56, Claim 8, "ethyleneglycol" should read --ethylene glycol--.